(12) United States Patent
Bencivenga et al.

(10) Patent No.: US 11,117,883 B2
(45) Date of Patent: Sep. 14, 2021

(54) BENZIMIDAZOLE COMPOUNDS AS C-KIT INHIBITORS

(71) Applicant: Ariad Pharmaceuticals, Inc., Cambridge, MA (US)

(72) Inventors: Nicholas E. Bencivenga, Cambridge, MA (US); David C. Dalgarno, Cambridge, MA (US); Joseph M. Gozgit, Cambridge, MA (US); Wei-Sheng Huang, Cambridge, MA (US); Anna Kohlmann, Cambridge, MA (US); Feng Li, Cambridge, MA (US); Jiwei Qi, Cambridge, MA (US); William C. Shakespeare, Cambridge, MA (US); Ranny M. Thomas, Cambridge, MA (US); Yihan Wang, Cambridge, MA (US); Yun Zhang, Cambridge, MA (US); Xiaotian Zhu, Cambridge, MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 51 days.

(21) Appl. No.: 16/469,535

(22) PCT Filed: Dec. 14, 2017

(86) PCT No.: PCT/US2017/066299
§ 371 (c)(1),
(2) Date: Jun. 13, 2019

(87) PCT Pub. No.: WO2018/112140
PCT Pub. Date: Jun. 21, 2018

(65) Prior Publication Data
US 2020/0039958 A1    Feb. 6, 2020

Related U.S. Application Data

(60) Provisional application No. 62/434,839, filed on Dec. 15, 2016.

(51) Int. Cl.
| | |
|---|---|
| *A61K 31/4184* | (2006.01) |
| *A61K 31/4178* | (2006.01) |
| *A61K 31/4439* | (2006.01) |
| *A61K 31/4427* | (2006.01) |
| *C07D 403/14* | (2006.01) |
| *C07D 403/12* | (2006.01) |
| *C07D 403/04* | (2006.01) |
| *C07D 401/14* | (2006.01) |
| *C07D 401/12* | (2006.01) |
| *C07D 413/14* | (2006.01) |
| *C07D 405/14* | (2006.01) |

(52) U.S. Cl.
CPC ......... *C07D 401/14* (2013.01); *C07D 401/12* (2013.01); *C07D 403/04* (2013.01); *C07D 403/12* (2013.01); *C07D 403/14* (2013.01); *C07D 405/14* (2013.01); *C07D 413/14* (2013.01)

(58) Field of Classification Search
CPC ............ A61K 31/4184; A61K 31/4178; A61K 31/4439; A61K 31/4427; C07D 403/14; C07D 403/12; C07D 403/04; C07D 401/14; C07D 401/12; C07D 413/14; C07D 405/14; A61P 35/00
USPC ........... 514/394, 395, 397; 548/306.1, 304.7, 548/307.4, 335.1; 546/273.4, 272.7
See application file for complete search history.

(56) References Cited

U.S. PATENT DOCUMENTS 5,262,564 A    11/1993 Kun et al.

FOREIGN PATENT DOCUMENTS

| EP | 2896620 A1 | 7/2015 |
| EP | 2896620 A1 | 7/2015 |

OTHER PUBLICATIONS

International Search Report for PCT/US2017/066299, 4 pages (dated Apr. 17, 2018).
Corless, C. L. et al., "Gastrointestinal stromal tumours: origin and molecular oncology", National Reviews: Cancer, Nature Publishing Group, a division of Macmillan Publishers Limited, Nov. 17, 2011, vol. 11, pp. 865-878.
Demetri, G. D. et al., "Efficacy and safety of regorafenib for advanced gastrointestinal stromal tumours after failure of imatinib and sunitinib (GRID): an international, multicentre, randomised, placebo-controlled, phase 3 trial GRID", The Lancet, Jan. 26, 2013, vol. 381, pp. 295-302.

(Continued)

*Primary Examiner* — Joseph R Kosack
*Assistant Examiner* — Sagar Patel
(74) *Attorney, Agent, or Firm* — Proskauer Rose LLP; Fangli Chen

(57) ABSTRACT

The invention relates to c-Kit inhibitors useful in the treatment of cancers, and other serine-threonine kinase mediated diseases, having the Formula: (I) where A, L, $R_1$, $R_2$, $R_3$, and n are described herein.

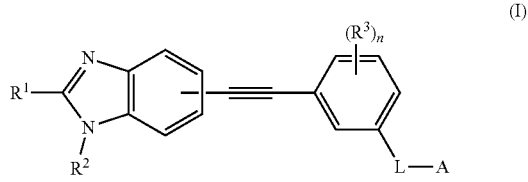

7 Claims, No Drawings

(56) References Cited

OTHER PUBLICATIONS

Demetri, G. D. et al., "Efficacy and safety of sunitinib in patients with advanced gastrointestinal stromal tumour after failure of imatinib: a randomised controlled trial", The Lancet, Oct. 14, 2006, vol. 368, Issue 9544, pp. 1329-1338.

George, S. et al., "Efficacy and Safety of Regorafenib in Patients With Metastatic and/or Unresectable GI Stromal Tumor After Failure of Imatinib and Sunitinib: A Multicenter Phase II Trial", Journal of Clinical Oncology, American Society of Clinical Oncology, Jul. 1, 2012, vol. 30, pp. 2401-2407.

Heinrich, M. C. et al., "Molecular correlates of imatinib resistance in gastrointestinal stromal tumors", Journal of Clinical Oncology, American Society of Clinical Oncology, Oct. 10, 2006, vol. 24, pp. 4764-4774.

Heinrich, M. C. et al., "Primary and Secondary Kinase Genotypes Correlate With the Biological and Clinical Activity of Sunitinib in Imatinib-Resistant Gastrointestinal Stromal Tumor", Journal of Clinical Oncology, American Society of Clinical Oncology, Nov. 1, 2008, vol. 26, pp. 5352-5359.

Huang, W. et al., "Discovery of 3-[2-(Imidazo[1,2-b]pyridazin-3-yl)ethynyl]-4-methyl-N-{4-[(4-methylpiperazin-1-yl)methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant", Journal of Medicinal Chemistry, Jun. 1, 2010, vol. 53, pp. 4701-4719.

International Preliminary Report on Patentability for PCT/US2017/066299 dated Jun. 18, 2019, 10 pages.

International Search Report for PCT/US2017/066299 dated Jun. 21, 2018, 5 pages.

Serrano-Garcia, C. et al., "In vitro and in vivo activity of regorafenib (REGO) in drug resistant gastrointestinal stromal tumors", Journal of Clinical Oncology, May 20, 2013, vol. 31, No. 15 (supplement), pp. 10510.

Wardelmann, E. et al., "Polyclonal evolution of multiple secondary KIT mutations in gastrointestinal stromal tumors under treatment with imatinib mesylate", Clinical Cancer Research, American Association for Cancer Research, Mar. 15, 2006, vol. 12, pp. 1743-1749.

Written Opinion for PCT/US2017/066299 dated Jun. 21, 2018, 9 pages.

Edling, Charlotte E. et al. "c-Kit—A hematopoietic cell essential receptor tyrosine kinase." International Journal of Biochemistry and Cell Biology (2007), 39(11):1995-8. doi:10.1016/j.biocel.2006.12.005.

BENZIMIDAZOLE COMPOUNDS AS C-KIT INHIBITORS

CROSS REFERENCE TO RELATED APPLICATIONS

This application is a 35 U.S.C. § 371 National Stage Application of International Application No. PCT/US2017/066299, filed Dec. 14, 2017, which claims priority to U.S. Provisional Patent Application Ser. No. 62/434,839 filed Dec. 15, 2016, the entirety of which is hereby incorporated by reference.

FIELD OF INVENTION

The present invention is directed to inhibitors of tyrosine-protein kinase Kit (c-Kit) useful in the treatment of diseases or disorders associated with c-Kit. Specifically, the invention is concerned with compounds and compositions inhibiting c-Kit, methods of treating diseases or disorders associated with c-Kit, and methods of synthesis of these compounds.

BACKGROUND OF THE INVENTION

The discovery that the tyrosine kinase inhibitor (TKI) imatinib inhibits Kit, and its introduction as a treatment, transformed the clinical management of gastrointestinal stromal tumors (GIST) (Corless, C. L. et al., *Nat. Rev. Cancer.* 2011; 11: 865-78). Nonetheless, most imatinib-treated patients ultimately relapse due to outgrowth of clones with secondary, drug-resistant KIT mutations (Heinrich, M. C., et al., *J. Clin. Oncol.* 2006; 24: 4764-74). Secondary mutations typically occur in the ATP binding pocket encoded by exons 13 and 14, and the activation loop (A-loop) encoded by exons 17 and 18. The challenge of treating imatinib resistant GISTs is compounded by mutational heterogeneity, as patients can harbor multiple different secondary mutations in distinct tumor lesions, or even within different regions of the same lesion (Wardelmann E., et al., *Clin. Cancer Res.* 2006; 12: 1743-9).

GIST patients with imatinib-resistant tumors are treated with sunitinib, which potently inhibits KIT ATP-pocket mutants (Heinrich, M. C., et al., J Clin Oncol 2008; 26: 5352-9). However, sunitinib is ineffective against A-loop mutants, which account for 50% of imatinib-resistance mutations. This may explain why overall response rates (ORR) are low (7%) and median progression-free survival (PFS) is short (6.2 months) (Demetri, G. D., et al., *Lancet* 2006; 368: 1329-38). Regorafenib was recently approved as third line therapy, but also shows only moderate activity, with ORR of 4.5% and median PFS of 4.8 months (Demetri, G. D., et al., *Lancet* 2013; 381: 295-302). The Kit inhibitory properties of regorafenib have not yet been analyzed extensively, but both clinical and initial preclinical data suggest a limited spectrum of sensitive KIT mutants (George, S., et al., *J. Clin. Oncol.* 2012; 30: 2401-7; Serrano-Garcia, C., et al., ASCO Meeting Abstracts 2013; 31(15_suppl): 10510). Thus, additional agents are needed to overcome resistance mutations in KIT, in particular those in the A-loop.

The Kit inhibitors imatinib, sunitinib and regorafenib are effective GIST therapies, though most patients develop resistance to these drugs due to somatic acquisition of polyclonal secondary Kit mutants. The lack of efficacy of any single agent against the complete set of potential ATP-binding pocket and A-loop secondary mutants makes achievement of prolonged complete disease control in late stage patients challenging. To address this unmet medical need, presented herein, are compounds that target a broad range of primary and secondary Kit mutants, including those within the A-loop.

SUMMARY OF THE INVENTION

The present disclosure provides novel benzimidazole compounds and pharmaceutically acceptable salts as effective c-Kit inhibitors.

A first aspect of the invention relates to compounds of Formula (I):

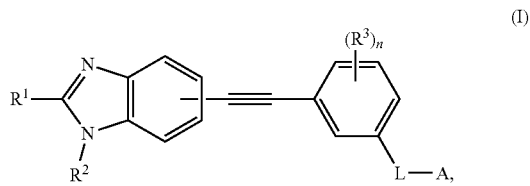

(I)

and pharmaceutically acceptable salts, hydrates, solvates, prodrugs, stereoisomers, and tautomers thereof, wherein:

L is —C(O)NR$^5$— or —NR$^5$C(O)—;

A is ($C_6$-$C_{10}$) aryl or 5- to 10-membered heteroaryl wherein the aryl or heteroaryl is optionally substituted with one or more R$^4$;

R$^1$ is H, ($C_1$-$C_6$) alkylamino, or ($C_1$-$C_6$) dialkylamino;

R$^2$ is H, ($C_1$-$C_6$) alkyl, —(C(R$^{6a}$)$_2$)$_p$—($C_3$-$C_7$) cycloalkyl, —(C(R$^{6a}$)$_2$)$_p$-heterocycloalkyl wherein the heterocycloalkyl comprises a 4- to 7-membered ring and 1 to 3 heteroatoms selected from N, O, and S, —(C(R$^{6a}$)$_2$)$_p$—($C_6$-$C_{10}$) aryl, or —(C(R$^{6a}$)$_2$)$_p$-heteroaryl wherein the heteroaryl comprises a 5- or 6-membered ring and 1 to 3 heteroatoms selected from N, O, and S, wherein the alkyl is optionally substituted with one or more R$^7$, wherein the cycloalkyl, heterocycloalkyl, aryl, or heteroaryl is optionally substituted with one or more R$^9$;

each R$^3$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, or OH;

each R$^4$ is independently at each occurrence ($C_1$-$C_6$) alkyl, ($C_1$-$C_6$) alkoxy, ($C_1$-$C_6$) haloalkyl, ($C_1$-$C_6$) haloalkoxy, halogen, —OH, CN, ($C_3$-$C_7$) cycloalkyl, —(C(R$^{6b}$)$_2$)$_q$—NH$_2$, —(C(R$^{6b}$)$_2$)$_q$—($C_1$-$C_6$) alkylamino, —(C(R$^{6b}$)$_2$)$_q$—($C_1$-$C_6$) dialkylamino, —(C(R$^{6b}$)$_2$)$_q$-heterocycloalkyl wherein the heterocycloalkyl comprises a 4- to 7-membered ring and 1 to 3 heteroatoms selected from N, O, and S, or —(C(R$^{6b}$)$_2$)$_q$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from ($C_1$-$C_6$) alkyl, —NH$_2$, ($C_1$-$C_6$) alkylamino, and ($C_1$-$C_6$) dialkylamino;

R$^5$ is H, ($C_1$-$C_6$) alkyl, or ($C_1$-$C_6$) haloalkyl;

each R$^{6a}$ and R$^{6b}$ is independently H or ($C_1$-$C_6$) alkyl;

R$^7$ is ($C_1$-$C_6$) alkoxy, ($C_1$-$C_6$) haloalkoxy, —OH, —NH$_2$, ($C_1$-$C_6$) alkylamino, ($C_1$-$C_6$) dialkylamino, or —C(O)N(R$^8$)$_2$;

each R$^8$ is independently H, ($C_1$-$C_6$) alkyl, or ($C_1$-$C_6$) haloalkyl;

each R$^9$ is independently at each occurrence ($C_1$-$C_6$) alkyl, ($C_1$-$C_6$) haloalkyl, —C(O)H, —C(O)($C_1$-$C_6$) alkyl, or 5- to 7-membered heterocycloalkyl ring comprising 1 to 3 heteroatoms selected from N, O and S, wherein the heterocycloalkyl is optionally substituted with one or more substituents each independently selected from $(C_1-C_6)$ alkyl, —C(O)H, or —C(O)($C_1-C_6$) alkyl, and wherein the alkyl is optionally substituted with one or more substituents each independently selected from $(C_1-C_6)$ alkoxy, —OH, $(C_1-C_6)$ haloalkoxy, —NH$_2$, $(C_1-C_6)$ alkylamino, or $(C_1-C_6)$ dialkylamino; and each n, p, and q is independently 0, 1 or 2.

A second aspect of the invention relates to a method of treating a c-Kit-mediated disease or disorder. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of preventing a c-Kit-mediated disease or disorder. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inhibiting c-Kit. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a disease or disorder associated with inhibiting c-Kit. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of preventing a disease or disorder associated with inhibiting c-Kit. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting c-Kit.

Another aspect of the present invention relates to a compound of Formula (I), or a pharmaceutically acceptable salt, hydrate, solvate, prodrug, stereoisomer, or tautomer thereof, for use in the manufacture of a medicament for preventing a disease associated with inhibiting c-Kit.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting c-Kit.

Another aspect of the present invention relates to the use of a compound of Formula (I), or a pharmaceutically acceptable salt, hydrate, solvate, prodrug, stereoisomer, or tautomer thereof, in the prevention of a disease associated with inhibiting c-Kit.

The present invention further provides methods of treating or preventing a disease or disorder associated with modulation of c-Kit including, cancer and cell proliferative disorders, multiple sclerosis, asthma, inflammatory disorders, allergic reactions, fibrotic disorders, and metabolic disorders, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of c-Kit that are therapeutic agents in the treatment of diseases such as cancer and cell proliferative disorders, multiple sclerosis, asthma, inflammatory disorders, allergic reactions, fibrotic disorders, and metabolic disorders.

The present disclosure provides agents with novel mechanisms of action toward c-Kit enzymes in the treatment of various types of diseases including cancer and cell proliferative disorders, multiple sclerosis, asthma, mastocytosis, inflammatory disorders, allergic reactions, fibrotic disorders, auto-immune pathogenesis and metabolic disorders. Ultimately the present invention provides the medical community with a novel pharmacological strategy for the treatment of diseases and disorders associated with c-Kit.

DETAILED DESCRIPTION OF THE INVENTION

The present invention relates to compounds and compositions that are capable of inhibiting the activity of c-Kit. The invention features methods of treating, preventing or ameliorating a disease or disorder in which c-Kit plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of c-Kit dependent diseases and disorders by inhibiting the activity of c-Kit enzymes. Inhibition of c-Kit provides a novel approach to the treatment, prevention, or amelioration of diseases including, but not limited to, cancer and metastasis.

In a first aspect of the invention, the compounds of Formula (I) are described:

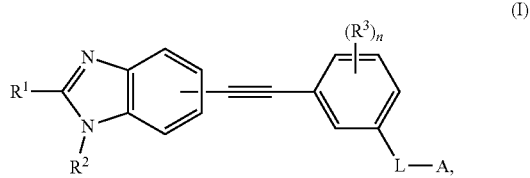

and pharmaceutically acceptable salts, hydrates, solvates, prodrugs, stereoisomers, and tautomers thereof, wherein A, L, $R_1$, $R_2$, $R_3$, and n are as described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—(C$_1$-C$_6$) alkyl, (C$_1$-C$_6$) alkyl, (C$_1$-C$_6$) alkoxy, (C$_1$-C$_6$) haloalkyl, (C$_1$-C$_6$) haloalkoxy, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)(C$_1$-C$_6$) alkyl, —OC(O)O(C$_1$-C$_6$) alkyl, —NH$_2$, —NH((C$_1$-C$_6$) alkyl), —N((C$_1$-C$_6$) alkyl)$_2$, —NHC(O)(C$_1$-C$_6$) alkyl, —C(O)NH(C$_1$-C$_6$) alkyl, —S(O)$_2$(C$_1$-C$_6$) alkyl, —S(O)NH(C$_1$-C$_6$) alkyl, and S(O)N((C$_1$-C$_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—(C$_1$-C$_6$) alkyl, (C$_1$-C$_6$) alkyl, —O—(C$_2$-C$_6$) alkenyl, —O—(C$_2$-C$_6$) alkynyl, (C$_2$-C$_6$) alkenyl, (C$_2$-C$_6$) alkynyl, —OH, —OP(O)(OH)$_2$, —OC(O)(C$_1$-C$_6$) alkyl, —C(O)(C$_1$-C$_6$) alkyl, —OC(O)O(C$_1$-C$_6$) alkyl, NH$_2$, NH((C$_1$-C$_6$) alkyl), N((C$_1$-C$_6$) alkyl)$_2$, —S(O)$_2$—(C$_1$-C$_6$) alkyl, —S(O)NH(C$_1$-C$_6$) alkyl, and S(O)N((C$_1$-C$_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a (C$_1$-C$_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptenyl, cyclooctanyl, norbornanyl, norbornenyl, bicyclo[2.2.2]octenyl, or bicyclo[2.2.2]octenyl.

"Heterocyclyl" or "heterocycloalkyl" monocyclic rings containing carbon and heteroatoms taken from oxygen, nitrogen, or sulfur and wherein there is not delocalized $\pi$ electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxolanyl, piperidinyl, morpholinyl, thiomorpholinyl, thiomorpholinyl S-oxide, thiomorpholinyl S-dioxide, piperazinyl, azepinyl, oxepanyl, diazepinyl, tropanyl, oxazolidinonyl, and homotropanyl.

The term "hydroxyalkyl" means an alkyl group as defined above, where the alkyl group is substituted with one or more —OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, NH$_2$, —NH(alkyl) or alkylamino, —N(alkyl)$_2$ or dialkylamino, amide-, carbamide-, urea, and sulfamide substituents are included in the term "amino".

The term "alkylamino" as used herein refers to an amino or NH$_2$ group where one of the hydrogens has been replaced with an alkyl group, as defined herein above, i.e., —NH(alkyl). Example of alkylamino groups include, but are not limited to, methylamino (i.e., —NH(CH$_3$)), ethylamino, propylamino, iso-propylamino, n-butylamino, sec-butylamino, tert-butylamino, etc.

The term "dialkylamino" as used herein refers to an amino or NH$_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N(CH$_3$)$_2$), diethylamino, dipropylamino, diiso-propyl amino, di-n-butylamino, di-sec-butylamino, di-tert-butylamino, methyl(ethyl)amino, methyl(butylamino), etc.

The term "oxo" as used herein refers to an "=O" group.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, "treating" or "treat" describes the management and care of a patient for the purpose of reversing, inhibiting, or combating a disease, condition, or disorder and includes the administration of a compound of the present disclosure (i.e., a compound of Formula (I), or a pharmaceutically acceptable salt, prodrug, metabolite, polymorph or solvate thereof, to reverse the disease, condition, or disorder, eliminate the disease, condition, or disorder, or inhibit the process of the disease, condition, or disorder.

A compound of the present disclosure (i.e., a compound of Formula (I), or a pharmaceutically acceptable salt, prodrug, metabolite, polymorph or solvate thereof, can also be used to prevent a disease, condition, or disorder or one or more symptoms of such disease, condition, or disorder. As used herein, "preventing" or "prevent" describes reducing or eliminating the onset of the symptoms or complications of the disease, condition, or disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting c-Kit, which are useful for the treatment of diseases and disorders associated with modulation of a c-Kit enzyme. The invention further relates to compounds, or pharmaceutically acceptable salts, hydrates, solvates, prodrugs, stereoisomers, or tautomers thereof, which are useful for inhibiting c-Kit.

In one embodiment, the compounds of Formula (I) have the structure of Formula (Ia):

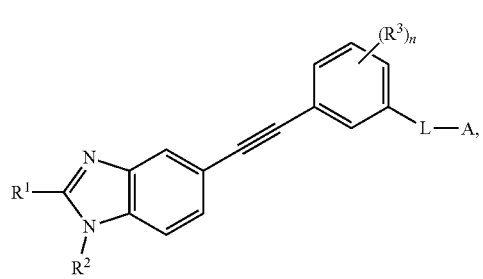

and pharmaceutically acceptable salts, hydrates, solvates, prodrugs, stereoisomers, and tautomers thereof.

In another embodiment, the compounds of Formula (I) have the structure of Formula (Ib):

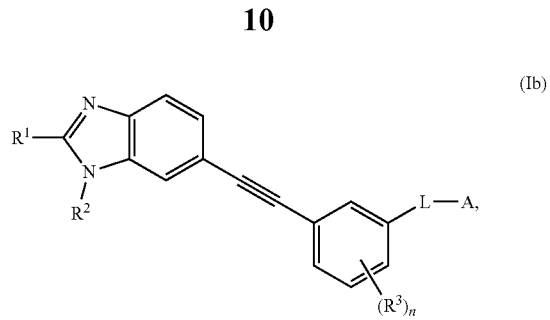

and pharmaceutically acceptable salts, hydrates, solvates, prodrugs, stereoisomers, and tautomers thereof.

In another embodiment, the compounds of Formula (I) have the structure of Formula (Ic):

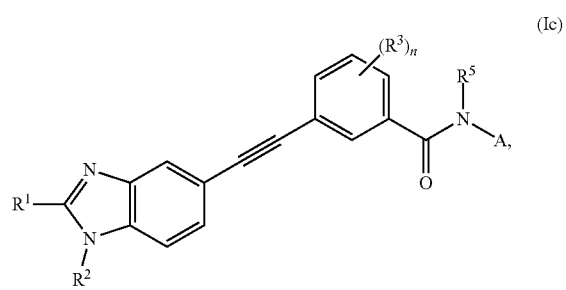

and pharmaceutically acceptable salts, hydrates, solvates, prodrugs, stereoisomers, and tautomers thereof.

In another embodiment, the compounds of Formula (I) have the structure of Formula (Id):

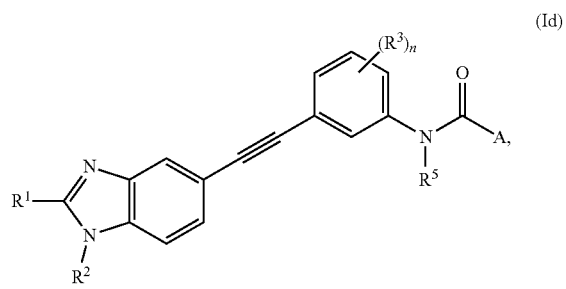

and pharmaceutically acceptable salts, hydrates, solvates, prodrugs, stereoisomers, and tautomers thereof.

In another embodiment, the compounds of Formula (I) have the structure of Formula (Ie):

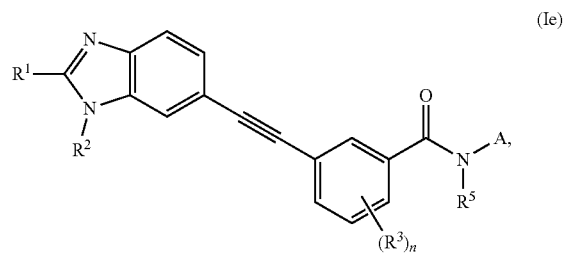

and pharmaceutically acceptable salts, hydrates, solvates, prodrugs, stereoisomers, and tautomers thereof.

In another embodiment, the compounds of Formula (I) have the structure of Formula (If):

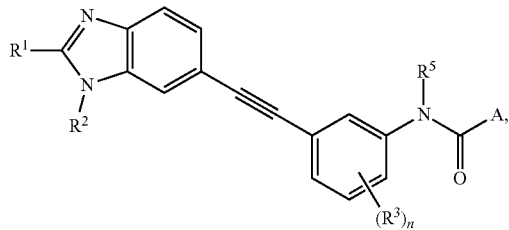

and pharmaceutically acceptable salts, hydrates, solvates, prodrugs, stereoisomers, and tautomers thereof.

In another embodiment, the compounds of Formula (I) have the structure of Formula (Ig):

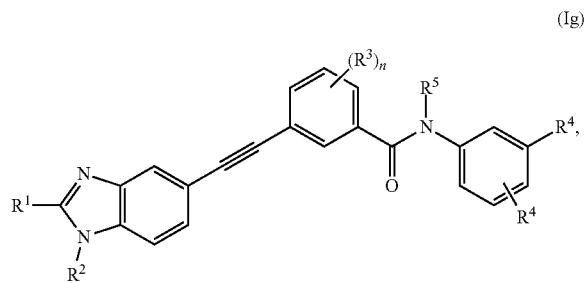

and pharmaceutically acceptable salts, hydrates, solvates, prodrugs, stereoisomers, and tautomers thereof.

In another embodiment, the compounds of Formula (I) have the structure of Formula (Ih):

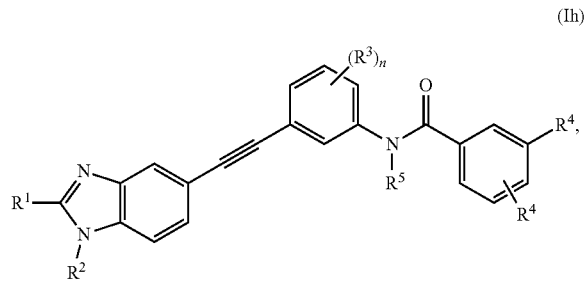

and pharmaceutically acceptable salts, hydrates, solvates, prodrugs, stereoisomers, and tautomers thereof.

In some embodiments of the Formulae above, A is $C_{6-10}$ aryl. In another embodiment, A is 5- or 6-membered heteroaryl. In yet another embodiment, A is 6-membered aryl. In another embodiment, A is 6-membered heteroaryl. In yet another embodiment, A is phenyl. In a further embodiment, A is pyridinyl.

In some embodiments of the Formulae above, L is —C(O)NR$^5$—. In another embodiment, L is —C(O)NH—.

In some embodiments of the Formulae above, L is —NR$^5$C(O)—. In another embodiment, L is —NHC(O)—.

In some embodiments of the Formulae above, R$^1$ is H, $(C_1-C_3)$ alkylamino, or $(C_1-C_3)$ dialkylamino. In another embodiment, R$^1$ is H, $(C_1-C_2)$ alkylamino, or $(C_1-C_2)$ dialkylamino. In another embodiment, R$^1$ is $(C_1-C_2)$ alkylamino, or $(C_1-C_2)$ dialkylamino. In another embodiment, R$^1$ is H.

In some embodiments of the Formulae above, R$^2$ is H, $(C_1-C_4)$ alkyl, —$(C(R^{6a})_2)_p$—$(C_3-C_7)$ cycloalkyl, —$(C(R^{6a})_2)_p$-heterocycloalkyl wherein the heterocycloalkyl comprises a 4- to 7-membered ring and 1 to 3 heteroatoms selected from N, O, and S, —$(C(R^{6a})_2)_p$—$(C_6-C_{10})$ aryl, or —$(C(R^{6a})_2)_p$-heteroaryl wherein the heteroaryl comprises a 5- or 6-membered ring and 1 to 3 heteroatoms selected from N, O, and S, wherein the alkyl is optionally substituted with one to four R$^7$, wherein the cycloalkyl, heterocycloalkyl, aryl, or heteroaryl is optionally substituted with one to four R$^9$. In another embodiment, R$^2$ is $(C_1-C_4)$ alkyl, —$(C(R^{6a})_2)_p$—$(C_3-C_7)$ cycloalkyl, —$(C(R^{6a})_2)_p$-heterocycloalkyl wherein the heterocycloalkyl comprises a 4- to 7-membered ring and 1 to 3 heteroatoms selected from N, O, and S, —$(C(R^{6a})_2)_p$—$(C_6-C_{10})$ aryl, or —$(C(R^{6a})_2)_p$-heteroaryl wherein the heteroaryl comprises a 5- or 6-membered ring and 1 to 3 heteroatoms selected from N, O, and S, wherein the alkyl is optionally substituted with one or more R$^7$, wherein the cycloalkyl, heterocycloalkyl, aryl, or heteroaryl is optionally substituted with one or more R$^9$. In another embodiment, R$^2$ is H or $(C_1-C_4)$ alkyl optionally substituted with one or more R$^7$. In another embodiment, R$^2$ is H, —$(C(R^{6a})_2)_p$—$(C_3-C_7)$ cycloalkyl, —$(C(R^{6a})_2)_p$-heterocycloalkyl wherein the heterocycloalkyl comprises a 4- to 7-membered ring and 1 to 3 heteroatoms selected from N, O, and S, —$(C(R^{6a})_2)_p$—$(C_6-C_{10})$ aryl, or —$(C(R^{6a})_2)_p$-heteroaryl wherein the heteroaryl comprises a 5- or 6-membered ring and 1 to 3 heteroatoms selected from N, O, and S, wherein the cycloalkyl, heterocycloalkyl, aryl, or heteroaryl is optionally substituted with one or more R$^9$.

In another embodiment, R$^2$ is H, $(C_1-C_4)$ alkyl, —$(CH_2)_p$—$(C_3-C_7)$ cycloalkyl, —$(CH_2)_p$-heterocycloalkyl wherein the heterocycloalkyl comprises a 4- to 7-membered ring and 1 to 3 heteroatoms selected from N, O, and S, —$(CH_2)_p$—$(C_6-C_{10})$ aryl, or —$(CH_2)_p$-heteroaryl wherein the heteroaryl comprises a 5- or 6-membered ring and 1 to 3 heteroatoms selected from N, O, and S, wherein the alkyl is optionally substituted with one or more R$^7$, wherein the cycloalkyl, heterocycloalkyl, aryl, or heteroaryl is optionally substituted with one or more R$^9$.

In another embodiment, R$^2$ is H, $(C_1-C_4)$ alkyl, —$(CH_2)_p$—$(C_3-C_7)$ cycloalkyl, —$(CH_2)_p$-heterocycloalkyl wherein the heterocycloalkyl comprises a 4- to 7-membered ring and 1 to 3 heteroatoms selected from N, O, and S, —$(CH_2)_p$—$(C_6-C_{10})$ aryl, or —$(CH_2)_p$-heteroaryl wherein the heteroaryl comprises a 5- or 6-membered ring and 1 to 3 heteroatoms selected from N, O, and S, wherein the alkyl is optionally substituted with one to four R$^7$, wherein the cycloalkyl, heterocycloalkyl, aryl, or heteroaryl is optionally substituted with one to four R$^9$.

In some embodiments of the Formulae above, each R$^3$ is independently at each occurrence $(C_1-C_3)$ alkyl, $(C_1-C_3)$ alkoxy, $(C_1-C_3)$ haloalkyl, $(C_1-C_3)$ haloalkoxy, halogen, or OH. In another embodiment, each R$^3$ is independently at each occurrence $(C_1-C_3)$ alkyl, $(C_1-C_3)$ alkoxy, $(C_1-C_3)$ haloalkyl, or $(C_1-C_3)$ haloalkoxy. In another embodiment, each R$^3$ is independently at each occurrence halogen or OH. In another embodiment, each R$^3$ is independently at each occurrence $(C_1-C_3)$ alkyl, $(C_1-C_3)$ alkoxy, halogen, or OH. In another embodiment, each R$^3$ is independently at each occurrence $(C_1-C_3)$ haloalkyl, $(C_1-C_3)$ haloalkoxy, halogen, or OH. In another embodiment, each R$^3$ is independently at each occurrence $(C_1-C_3)$ alkyl, $(C_1-C_3)$ alkoxy, or halogen. In another embodiment, each R$^3$ is independently at each occurrence $(C_1-C_3)$ alkyl or halogen. In another embodiment, each R$^3$ is independently at each occurrence $(C_1-C_2)$ alkyl or halogen.

In some embodiments of the Formulae above, each $R^4$ is independently at each occurrence $(C_1\text{-}C_3)$ alkyl, $(C_1\text{-}C_3)$ alkoxy, $(C_1\text{-}C_3)$ haloalkyl, $(C_1\text{-}C_3)$ haloalkoxy, halogen, —OH, CN, $(C_3\text{-}C_7)$ cycloalkyl, —$C(R^{6b})_2)_q$—$NH_2$, —$(C(R^{6b})_2)_q$—$(C_1\text{-}C_6)$ alkylamino, —$(C(R^{6b})_2)_q$—$(C_1\text{-}C_6)$ dialkylamino, —$(C(R^{6b})_2)_q$-heterocycloalkyl wherein the heterocycloalkyl comprises a 4- to 7-membered ring and 1 to 3 heteroatoms selected from N, O, and S, or —$(C(R^{6b})_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from $(C_1\text{-}C_6)$ alkyl, —$NH_2$, $(C_1\text{-}C_6)$ alkylamino, and $(C_1\text{-}C_6)$ dialkylamino. In another embodiment, each $R^4$ is independently at each occurrence $(C_1\text{-}C_3)$ alkyl, $(C_1\text{-}C_3)$ alkoxy, $(C_1\text{-}C_3)$ haloalkyl, $(C_1\text{-}C_3)$ haloalkoxy, halogen, —OH, CN, $(C_3\text{-}C_7)$ cycloalkyl, —$(C(R^{6b})_2)_q$—$NH_2$, —$(C(R^{6b})_2)_q$—$(C_1\text{-}C_6)$ alkylamino, —$(C(R^{6b})_2)_q$—$(C_1\text{-}C_6)$ dialkylamino, —$(C(R^{6b})_2)_q$-heterocycloalkyl wherein the heterocycloalkyl comprises a 4- to 7-membered ring and 1 to 3 heteroatoms selected from N, O, and S, or —$(C(R^{6b})_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one to four substituents each independently selected from $(C_1\text{-}C_6)$ alkyl, —$NH_2$, $(C_1\text{-}C_6)$ alkylamino, and $(C_1\text{-}C_6)$ dialkylamino.

In another embodiment, each $R^4$ is independently at each occurrence $(C_1\text{-}C_3)$ alkoxy, $(C_1\text{-}C_3)$ haloalkoxy, halogen, CN, $(C_3\text{-}C_7)$ cycloalkyl, —$(C(R^{6b})_2)_q$—$NH_2$, —$(C(R^{6b})_2)_q$—$(C_1\text{-}C_6)$ alkylamino, —$(C(R^{6b})_2)_q$—$(C_1\text{-}C_6)$ dialkylamino, —$(C(R^{6b})_2)_q$-heterocycloalkyl wherein the heterocycloalkyl comprises a 4- to 7-membered ring and 1 to 3 heteroatoms selected from N, O, and S, or —$(C(R^{6b})_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one to four substituents each independently selected from $(C_1\text{-}C_6)$ alkyl, —$NH_2$, $(C_1\text{-}C_6)$ alkylamino, and $(C_1\text{-}C_6)$ dialkylamino.

In another embodiment, each $R^4$ is independently at each occurrence $(C_1\text{-}C_3)$ alkoxy, $(C_1\text{-}C_3)$ haloalkoxy, halogen, CN, $(C_3\text{-}C_7)$ cycloalkyl, —$(C(R^{6b})_2)_q$—$NH_2$, —$(C(R^{6b})_2)_q$—$(C_1\text{-}C_6)$ alkylamino, —$(C(R^{6b})_2)_q$—$(C_1\text{-}C_6)$ dialkylamino, —$(C(R^{6b})_2)_q$-heterocycloalkyl wherein the heterocycloalkyl comprises a 4- to 7-membered ring and 1 to 3 heteroatoms selected from N, O, and S, or —$(C(R^{6b})_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one to four substituents each independently selected from $(C_1\text{-}C_6)$ alkyl, —$NH_2$, $(C_1\text{-}C_6)$ alkylamino, and $(C_1\text{-}C_6)$ dialkylamino.

In another embodiment, each $R^4$ is independently at each occurrence $(C_1\text{-}C_3)$ haloalkoxy, CN, $(C_3\text{-}C_7)$ cycloalkyl, —$(C(R^{6b})_2)_q$—$NH_2$, —$(C(R^{6b})_2)_q$—$(C_1\text{-}C_6)$ alkylamino, —$(C(R^{6b})_2)_q$—$(C_1\text{-}C_6)$ dialkylamino, —$(C(R^{6b})_2)_q$-heterocycloalkyl wherein the heterocycloalkyl comprises a 4- to 7-membered ring and 1 to 3 heteroatoms selected from N, O, and S, or —$(C(R^{6b})_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one to four substituents each independently selected from $(C_1\text{-}C_6)$ alkyl, —$NH_2$, $(C_1\text{-}C_6)$ alkylamino, and $(C_1\text{-}C_6)$ dialkylamino. In another embodiment, each $R^4$ is independently at each occurrence $(C_1\text{-}C_3)$ haloalkoxy, CN, $(C_3\text{-}C_7)$ cycloalkyl, —$(CH_2)_q$—$NH_2$, —$(CH_2)_q$—$(C_1\text{-}C_6)$ alkylamino, —$(CH_2)_q$—$(C_1\text{-}C_6)$ dialkylamino, —$(CH_2)_q$-heterocycloalkyl wherein the heterocycloalkyl comprises a 4- to 7-membered ring and 1 to 3 heteroatoms selected from N, O, and S, or —$(CH_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one to four substituents each independently selected from $(C_1\text{-}C_6)$ alkyl, —$NH_2$, $(C_1\text{-}C_6)$ alkylamino, and $(C_1\text{-}C_6)$ dialkylamino.

In some embodiments of the Formulae above, $R^5$ is H, $(C_1\text{-}C_3)$ alkyl, or $(C_1\text{-}C_3)$ haloalkyl. In another embodiment, $R^5$ is $(C_1\text{-}C_3)$ alkyl, or $(C_1\text{-}C_3)$ haloalkyl. In another embodiment, $R^5$ is H or $(C_1\text{-}C_3)$ alkyl. In another embodiment, $R^5$ is H, methyl, ethyl, n-propyl, or i-propyl. In another embodiment, $R^5$ is H, methyl, or ethyl. In another embodiment, $R^5$ is methyl or ethyl. In another embodiment, $R^5$ is H.

In some embodiments of the Formulae above, $R^{6a}$ is H or $(C_1\text{-}C_3)$ alkyl. In another embodiment, $R^{6a}$ is H or $(C_1\text{-}C_2)$ alkyl. In another embodiment, $R^{6a}$ is $(C_1\text{-}C_3)$ alkyl. In another embodiment, $R^{6a}$ is H.

In some embodiments of the Formulae above, $R^{6b}$ is H or $(C_1\text{-}C_3)$ alkyl. In another embodiment, $R^{6b}$ is H or $(C_1\text{-}C_2)$ alkyl. In another embodiment, $R^{6b}$ is $(C_1\text{-}C_3)$ alkyl. In another embodiment, $R^{6b}$ is H.

In some embodiments of the Formulae above, $R^7$ is $(C_1\text{-}C_3)$ alkoxy, $(C_1\text{-}C_3)$ haloalkoxy, —OH, —$NH_2$, $(C_1\text{-}C_3)$ alkylamino, $(C_1\text{-}C_3)$ dialkylamino, or —$C(O)N(R^8)_2$. In another embodiment, $R^7$ is $(C_1\text{-}C_3)$ alkoxy, —OH, —$NH_2$, $(C_1\text{-}C_3)$ alkylamino, $(C_1\text{-}C_3)$ dialkylamino, or —$C(O)N(R^8)_2$. In another embodiment, $R^7$ is $(C_1\text{-}C_3)$ alkoxy, $(C_1\text{-}C_3)$ alkylamino, $(C_1\text{-}C_3)$ dialkylamino, or —$C(O)N(R^8)_2$. In another embodiment, $R^7$ is $(C_1\text{-}C_3)$ alkoxy, $(C_1\text{-}C_3)$ dialkylamino, or —$C(O)N(R^8)_2$.

In some embodiments of the Formulae above, $R^8$ is independently H, $(C_1\text{-}C_3)$ alkyl, or $(C_1\text{-}C_3)$ haloalkyl. In another embodiment, $R^8$ is $(C_1\text{-}C_3)$ alkyl, or $(C_1\text{-}C_3)$ haloalkyl. In another embodiment, $R^8$ is H or $(C_1\text{-}C_3)$ alkyl. In another embodiment, $R^8$ is H, methyl, ethyl, n-propyl, or i-propyl. In another embodiment, $R^8$ is methyl or ethyl. In another embodiment, $R^8$ is H. In another embodiment, $R^8$ is H, methyl, or ethyl.

In some embodiments of the Formulae above, each $R^9$ is independently at each occurrence $(C_1\text{-}C_3)$ alkyl, $(C_1\text{-}C_3)$ haloalkyl, —$C(O)H$, —$C(O)(C_1\text{-}C_3)$ alkyl, or 5- to 7-membered heterocycloalkyl ring comprising 1 to 3 heteroatoms selected from N, O and S, wherein the heterocycloalkyl is optionally substituted with one to four substituents each independently selected from $(C_1\text{-}C_6)$ alkyl, —$C(O)H$, or —$C(O)(C_1\text{-}C_6)$ alkyl, and wherein the alkyl is optionally substituted with one to four substituents each independently selected from $(C_1\text{-}C_6)$ alkoxy, —OH, $(C_1\text{-}C_6)$ haloalkoxy, —$NH_2$, $(C_1\text{-}C_6)$ alkylamino, or $(C_1\text{-}C_6)$ dialkylamino.

In another embodiment, each $R^9$ is independently at each occurrence $(C_1\text{-}C_3)$ alkyl, —$C(O)(C_1\text{-}C_3)$ alkyl, or 5- to 7-membered heterocycloalkyl ring comprising 1 to 3 heteroatoms selected from N, O and S, wherein the heterocycloalkyl is optionally substituted with one to four substituents each independently selected from $(C_1\text{-}C_6)$ alkyl, —$C(O)H$, or —$C(O)(C_1\text{-}C_6)$ alkyl, and wherein the alkyl is optionally substituted with one to four substituents each independently selected from $(C_1\text{-}C_6)$ alkoxy, —OH, $(C_1\text{-}C_6)$ haloalkoxy, —$NH_2$, $(C_1\text{-}C_6)$ alkylamino, or $(C_1\text{-}C_6)$ dialkylamino. In another embodiment, each $R^9$ is independently at each occurrence $(C_1\text{-}C_3)$ alkyl or 5- to 7-membered heterocycloalkyl ring comprising 1 to 3 heteroatoms selected from N, O and S, wherein the heterocycloalkyl is optionally substituted with one to four substituents each independently selected from $(C_1$-$C_6)$ alkyl, —C(O)H, or —C(O)$(C_1$-$C_6)$ alkyl, and wherein the alkyl is optionally substituted with one to four substituents each independently selected from $(C_1$-$C_6)$ alkoxy, —OH, $(C_1$-$C_6)$ haloalkoxy, —NH$_2$, $(C_1$-$C_6)$ alkylamino, or $(C_1$-$C_6)$ dialkylamino.

In another embodiment, each $R^9$ is independently at each occurrence $(C_1$-$C_3)$ alkyl or 5- to 7-membered heterocycloalkyl ring comprising 1 to 3 heteroatoms selected from N, O and S, wherein the heterocycloalkyl is optionally substituted with one to four substituents each independently selected from $(C_1$-$C_6)$ alkyl, —C(O)H, or —C(O)$(C_1$-$C_6)$ alkyl, and wherein the alkyl is optionally substituted with one to four substituents each independently selected from $(C_1$-$C_6)$ alkoxy, —OH, or $(C_1$-$C_6)$ dialkylamino.

In some embodiments of the Formulae above, n is 0, 1 or 2. In another embodiment, n is 0 or 1. In another embodiment, n is 1 or 2. In yet another embodiment, n is 0. In yet another embodiment, n is 1. In another embodiment, n is 2.

In some embodiments of the Formulae above, p is 0, 1, or 2. In another embodiment, p is 0 or 1. In another embodiment, p is 1 or 2. In yet another embodiment, p is 0. In another embodiment, p is 1. In another embodiment, p is 2.

In some embodiments of the Formulae above, q is 0, 1, or 2. In another embodiment, q is 0 or 1. In another embodiment, q is 1 or 2. In yet another embodiment, q is 0. In another embodiment, q is 1. In another embodiment, q is 2.

In some embodiments of the Formulae above, L is a —C(O)NR$^5$—.

In some embodiments of the Formulae above, L is a —NR$^5$C(O)—.

In some embodiments of the Formulae above, R$^3$ is $(C_1$-$C_6)$ alkyl or halogen.

In some embodiments of the Formulae above, R$^3$ is methyl or F.

In some embodiments of the Formulae above, R$^3$ is methyl.

In some embodiments of the Formulae above, R$^1$ is H.

In some embodiments of the Formulae above, A is $(C_6$-$C_{10})$ aryl optionally substituted with one or two R$^4$.

In some embodiments of the Formulae above, A is 6-membered heteroaryl optionally substituted with one or two R$^4$;

In some embodiments of the Formulae above, A is phenyl or pyridinyl optionally substituted with one or two R$^4$.

In some embodiments of the Formulae above, A is phenyl or pyridinyl substituted with one R$^4$.

In some embodiments of the Formulae above, A is phenyl or pyridinyl substituted with two R$^4$.

In some embodiments of the Formulae above, R$^5$ is H.

In some embodiments of the Formulae above, n is 0.

In some embodiments of the Formulae above, n is 1.

In some embodiments of the Formulae above, A is phenyl or pyridinyl substituted with one R$^4$ and R$^4$ is CF$_3$ or cyclopropyl.

In some embodiments of the Formulae above, A is phenyl or pyridinyl substituted with two R$^4$ and at least one R$^4$ is CF$_3$.

In some embodiments of the Formulae above, n is 1 and R$^3$ is methyl.

In some embodiments of the Formulae above, R$^1$ is H.

In some embodiments of the Formulae above, one R$^4$ is $(C_1$-$C_6)$ haloalkyl and the other R$^4$ is CN, —(CH$_2$)—$(C_1$-$C_6)$ dialkylamino, -heterocycloalkyl or —(CH$_2$)-heterocycloalkyl wherein the heterocycloalkyl comprises a 4- to 7-membered ring and 1 to 3 heteroatoms selected from N, O, and S, wherein the heterocycloalkyl is optionally substituted with one or more $(C_1$-$C_3)$ alkyl.

In some embodiments of the Formulae above, one R$^4$ is CF$_3$ and the other R$^4$ is CN, —(CH$_2$)—$(C_1$-$C_6)$ dialkylamino, -heterocycloalkyl or —(CH$_2$)-heterocycloalkyl wherein the heterocycloalkyl comprises a 4- to 7-membered ring and 1 to 3 heteroatoms selected from N, O, and S, wherein the heterocycloalkyl is optionally substituted with one or more $(C_1$-$C_3)$ alkyl.

In some embodiments of the Formulae above, one R$^4$ is CF$_3$ and the other R$^4$ is CN, —(CH$_2$)—N(CH$_3$)$_2$, piperazinyl, —(CH$_2$)-piperazinyl, —(CH$_2$)-morpholinyl, or —(CH$_2$)-pyrrolidinyl, wherein the piperazinyl, morpholino, or pyrrolidinyl is optionally substituted with one or more $(C_1$-$C_3)$ alkyl.

In some embodiments of the Formulae above, one R$^2$ is $(C_1$-$C_6)$ alkyl or —(C(R$^{6b}$)$_2$)$_q$-heteroaryl wherein the heteroaryl comprises a 5- or 6-membered ring and 1 to 3 heteroatoms selected from N, O, and S and is substituted with one to two $(C_1$-$C_6)$ alkyl.

In some embodiments of the Formulae above, one R$^2$ is CH$_3$ or heteroaryl wherein the heteroaryl comprises a 5- or 6-membered ring and 1 to 3 heteroatoms selected from N, O, and S and substituted with one to two $(C_1$-$C_6)$ alkyl.

In some embodiments of the Formulae above, one R$^2$ is CH$_3$ or pyrazolyl substituted with one to two $(C_1$-$C_6)$ alkyl.

In some embodiments of the Formulae above, R$^4$ is $(C_1$-$C_6)$ haloalkyl.

In some embodiments of the Formulae above, R$^4$ is CF$_3$.

In some embodiments of the Formulae above, n is 1, R$^3$ is methyl, R$^1$ is H, and R$^2$ is H; CH$_3$; CH$_2$CH$_3$; —(CH$_2$)$_2$N(CH$_3$)$_2$; —(CH$_2$)$_3$N(CH$_3$)$_2$; —CH$_2$C(O)NH(CH$_3$); —(CH$_2$)$_2$morpholinyl; —(CH$_2$)$_2$OCH$_3$; piperidinyl substituted with methyl; phenyl optionally substituted with 4-methylpiperazine; —CH$_2$-pyridinyl; cyclopropyl; triazolyl substituted with methyl; or imidazolyl substituted with methyl or N-methyl piperidinyl.

In some embodiments of the Formulae above, n is 1 and R$^3$ is methyl, R$^1$ is pyrazolyl optionally substituted with methyl; —(CH$_2$)$_2$OH; —(CH$_2$)$_2$OCH$_3$; —(CH$_2$)$_2$N(CH$_3$)$_2$; —(CH$_2$)$_2$N(CH$_2$CH$_3$)$_2$; morpholinyl; or piperidinyl optionally substituted with methyl or —C(O)H.

In some embodiments of the Formulae above, n is 0 or 1 and R$^3$ is F, R$^1$ is pyrazolyl optionally substituted with methyl.

In some embodiments of the Formulae above, n is 1, R$^3$ is methyl, R$^1$ is NH$_2$ and R$^2$ is H.

In some embodiments of the Formulae above, L is —C(O)NR$^5$— and A is $(C_6$-$C_{10})$ aryl optionally substituted with one to four R$^4$. In another embodiment, L is —C(O)NR$^5$—, A is $(C_6$-$C_{10})$ aryl optionally substituted with one to four R$^4$, and R$_1$ is H. In another embodiment, L is —C(O)NR$^5$—, A is $(C_6$-$C_{10})$ aryl optionally substituted with one to four R$^4$, R$_1$ is H, and R$_3$ is $(C_1$-$C_6)$ alkyl, or halogen. In another embodiment, L is —C(O)NR$^5$—, A is $(C_6$-$C_{10})$ aryl optionally substituted with one to four R$^4$, R$_1$ is H, R$_3$ is $(C_1$-$C_6)$ alkyl, or halogen, and n is 1. In another embodiment, L is —C(O)NR$^5$—, A is $(C_6$-$C_{10})$ aryl optionally substituted with one to four R$^4$, R$_1$ is H, R$_3$ is $(C_1$-$C_6)$ alkyl, or halogen, n is 1, and R$^5$ is H. In another embodiment, L is —C(O)NR$^5$—, A is $(C_6$-$C_{10})$ aryl optionally substituted with one to four R$^4$, R$_1$ is H, and n is 0. In another embodiment, L is —C(O)NR$^5$—, A is $(C_6$-$C_{10})$ aryl optionally substituted with one to four R$^4$, R$_1$ is H, n is 0, and R$^5$ is H.

In some embodiments of the Formulae above, L is —C(O)NR$^5$— and A is 5- to 10-membered heteroaryl optionally substituted with one to four R$^4$. In another embodiment, L is —C(O)NR$^5$—, A is 5- to 10-membered heteroaryl optionally substituted with one to four R$^4$, and R$_1$ is H. In another embodiment, L is —C(O)NR$^5$—, A is 5- to 10-membered heteroaryl optionally substituted with one to four R$^4$, R$_1$ is H, and R$_3$ is (C$_1$-C$_6$) alkyl, or halogen. In another embodiment, L is —C(O)NR$^5$—, A is 5- to 10-membered heteroaryl optionally substituted with one to four R$^4$, R$_1$ is H, R$_3$ is (C$_1$-C$_6$) alkyl, or halogen, and n is 1. In another embodiment, L is —C(O)NR$^5$—, A is 5- to 10-membered heteroaryl optionally substituted with one to four R$^4$, R$_1$ is H, R$_3$ is (C$_1$-C$_6$) alkyl, or halogen, n is 1, and R$^5$ is H. In another embodiment, L is —C(O)NR$^5$—, A is 5- to 10-membered heteroaryl optionally substituted with one to four R$^4$, R$_1$ is H, and n is 0. In another embodiment, L is —C(O)NR$^5$—, A is 5- to 10-membered heteroaryl optionally substituted with one to four R$^4$, R$_1$ is H, n is 0, and R$^5$ is H.

In some embodiments of the Formulae above, L is —NR$^5$C(O)— and A is (C$_6$-C$_{10}$) aryl optionally substituted with one to four R$^4$. In another embodiment, L is —NR$^5$C(O)—, A is (C$_6$-C$_{10}$) aryl optionally substituted with one to four R$^4$, and R$_1$ is H. In another embodiment, L is —NR$^5$C(O)—, A is (C$_6$-C$_{10}$) aryl optionally substituted with one to four R$^4$, R$_1$ is H, and R$_3$ is (C$_1$-C$_6$) alkyl, or halogen. In another embodiment, L is —NR$^5$C(O)—, A is (C$_6$-C$_{10}$) aryl optionally substituted with one to four R$^4$, R$_1$ is H. R$_3$ is (C$_1$-C$_6$) alkyl, or halogen, and n is 1. In another embodiment, L is —NR$^5$C(O)—, A is (C$_6$-C$_{10}$) aryl optionally substituted with one to four R$^4$, R$_1$ is H. R$_3$ is (C$_1$-C$_6$) alkyl, or halogen, n is 1, and, and R$^5$ is H. In another embodiment, L is —NR$^5$C(O)—, A is (C$_6$-C$_{10}$) aryl optionally substituted with one to four R$^4$, R$_1$ is H, and n is 0. In another embodiment, L is —NR$^5$C(O)—, A is (C$_6$-C$_{10}$) aryl optionally substituted with one to four R$^4$, R$_1$ is H, n is 0, and R$^5$ is H.

In some embodiments of the Formulae above, L is —NR$^5$C(O)— and A is 5- to 10-membered heteroaryl optionally substituted with one to four R$^4$. In another embodiment, L is —NR$^5$C(O)—, A is 5- to 10-membered heteroaryl optionally substituted with one to four R$^4$, and R$_1$ is H. In another embodiment, L is —NR$^5$C(O)—, A is 5- to 10-membered heteroaryl optionally substituted with one to four R$^4$, R$_1$ is H, and R$_3$ is (C$_1$-C$_6$) alkyl, or halogen. In another embodiment, L is —NR$^5$C(O)—, A is 5- to 10-membered heteroaryl optionally substituted with one to four R$^4$, R$_1$ is H, R$_3$ is (C$_1$-C$_6$) alkyl, or halogen, and n is 1. In another embodiment, L is —NR$^5$C(O)—, A is 5- to 10-membered heteroaryl optionally substituted with one to four R$^4$, R$_1$ is H, R$_3$ is (C$_1$-C$_6$) alkyl, or halogen, n is 1, and R$^5$ is H. In another embodiment, L is —NR$^5$C(O)—, A is 5- to 10-membered heteroaryl optionally substituted with one to four R$^4$, R$_1$ is H, and n is 0. In another embodiment, L is —NR$^5$C(O)—, A is 5- to 10-membered heteroaryl optionally substituted with one to four R$^4$, R$_1$ is H, n is 0, and R$^5$ is H.

Non-limiting illustrative compounds of the invention include:
4-Methyl-3-((1-(2-(methylamino)-2-oxoethyl)-1H-benzo[d]imidazol-5-yl)ethynyl)-N-(4-(trifluoromethyl)pyridin-2-yl)benzamide (I-1);
3-((1H-benzo[d]imidazol-5-yl)ethynyl)-4-methyl-N-(4-(trifluoromethyl)pyridin-2-yl)benzamide (I-2);
3-((1-(2-(dimethylamino)ethyl)-1H-benzo[d]imidazol-5-yl)ethynyl)-4-methyl-N-(4-(trifluoromethyl)pyridin-2-yl)benzamide (I-3);
3-((1-(2-methoxyethyl)-1H-benzo[d]imidazol-5-yl)ethynyl)-4-methyl-N-(4-(trifluoromethyl)pyridin-2-yl)benzamide (I-4);
4-methyl-3-((1-(2-morpholinoethyl)-1H-benzo[d]imidazol-5-yl)ethynyl)-N-(4-(trifluoromethyl)pyridin-2-yl)benzamide (I-5);
3-((1-(3-(dimethylamino)propyl)-1H-benzo[d]imidazol-5-yl)ethynyl)-4-methyl-N-(4-(trifluoromethyl)pyridin-2-yl)benzamide (I-6);
3-((1-ethyl-H-benzo[d]imidazol-5-yl)ethynyl)-4-methyl-N-(4-(trifluoromethyl)pyridin-2-yl)benzamide (I-7);
4-methyl-3-((1-methyl-1H-benzo[d]imidazol-5-yl)ethynyl)-N-(4-(trifluoromethyl)pyridin-2-yl)benzamide (I-8);
3-((2-amino-1H-benzo[d]imidazol-6-yl)ethynyl)-4-methyl-N-(4-(trifluoromethyl)pyridin-2-yl)benzamide (I-10);
4-methyl-3-((1-methyl-1H-benzo[d]imidazol-6-yl)ethynyl)-N-(4-(trifluoromethyl)pyridin-2-yl)benzamide (I-11);
4-methyl-3-((1-(pyridin-3-ylmethyl)-1H-benzo[d]imidazol-5-yl)ethynyl)-N-(4-(trifluoromethyl)pyridin-2-yl)benzamide (I-12);
3-((1-cyclopropyl-1H-benzo[d]imidazol-5-yl)ethynyl)-4-methyl-N-(4-(trifluoromethyl)pyridin-2-yl)benzamide (I-13);
4-methyl-3-((1-(3-(4-methylpiperazin-1-yl)phenyl)-1H-benzo[d]imidazol-5-yl)ethynyl)-N-(4-(trifluoromethyl)pyridin-2-yl)benzamide (I-14);
4-methyl-3-((1-(4-(4-methylpiperazin-1-yl)phenyl)-1H-benzo[d]imidazol-5-yl)ethynyl)-N-(4-(trifluoromethyl)pyridin-2-yl)benzamide (I-15);
4-methyl-3-((1-(1-methyl-1H-pyrazol-4-yl)-1H-benzo[d]imidazol-5-yl)ethynyl)-N-(4-(trifluoromethyl)pyridin-2-yl)benzamide (I-17);
N-(4-methyl-3-((1-methyl-1H-benzo[d]imidazol-5-yl)ethynyl)phenyl)-4-((4-methylpiperazin-1-yl)methyl)-3-(trifluoromethyl)benzamide (I-18);
4-methyl-3-((1-(1-methyl-1H-pyrazol-4-yl)-1H-benzo[d]imidazol-5-yl)ethynyl)-N-(4-(trifluoromethyl)pyridin-2-yl)benzamide (I-19);
4-methyl-3-((1-(1-methylpiperidin-4-yl)-1H-benzo[d]imidazol-5-yl)ethynyl)-N-(4-(trifluoromethyl)pyridin-2-yl)benzamide (I-20);
4-methyl-3-((1-phenyl-1H-benzo[d]imidazol-5-yl)ethynyl)-N-(4-(trifluoromethyl)pyridin-2-yl)benzamide (I-21);
4-methyl-3-((1-methyl-1H-benzo[d]imidazol-5-yl)ethynyl)-N-(4-(4-methylpiperazin-1-yl)-3-(trifluoromethyl)phenyl)benzamide (I-22);
4-methyl-3-((1-(1-methyl-1H-imidazol-4-yl)-1H-benzo[d]imidazol-5-yl)ethynyl)-N-(4-(trifluoromethyl)pyridin-2-yl)benzamide (I-23);
4-methyl-3-((1-(1-methyl-1H-1,2,3-triazol-4-yl)-1H-benzo[d]imidazol-5-yl)ethynyl)-N-(4-(trifluoromethyl)pyridin-2-yl)benzamide (I-24);
3-((1-(1-(1-formylpiperidin-4-yl)-1H-pyrazol-4-yl)-1H-benzo[d]imidazol-5-yl)ethynyl)-4-methyl-N-(4-(trifluoromethyl)pyridin-2-yl)benzamide (I-25);
4-methyl-3-((1-(1-(piperidin-4-yl)-1H-pyrazol-4-yl)-1H-benzo[d]imidazol-5-yl)ethynyl)-N-(4-(trifluoromethyl)pyridin-2-yl)benzamide (I-26);
4-methyl-3-((1-(1-(1-methylpiperidin-4-yl)-1H-pyrazol-4-yl)-1H-benzo[d]imidazol-5-yl)ethynyl)-N-(4-(trifluoromethyl)pyridin-2-yl)benzamide (I-27);
N-(3-cyclopropylphenyl)-4-methyl-3-((1-(1-methyl-1H-pyrazol-4-yl)-1H-benzo[d]imidazol-5-yl)ethynyl)benzamide (I-28);
4-methyl-3-((1-(1-methyl-1H-pyrazol-4-yl)-1H-benzo[d]imidazol-5-yl)ethynyl)-N-(4-(pyrrolidin-1-ylmethyl)-3-(trifluoromethyl)phenyl)benzamide (I-29);
4-methyl-3-((1-methyl-1H-benzo[d]imidazol-5-yl)ethynyl)-N-(4-(pyrrolidin-1-ylmethyl)-3-(trifluoromethyl)phenyl)benzamide (I-30);

3-((1-(1-(2-hydroxyethyl)-1H-pyrazol-4-yl)-1H-benzo[d]imidazol-5-yl)ethynyl)-4-methyl-N-(4-(trifluoromethyl)pyridin-2-yl)benzamide (I-31);

3-((1-(1-(2-methoxyethyl)-1H-pyrazol-4-yl)-1H-benzo[d]imidazol-5-yl)ethynyl)-4-methyl-N-(4-(trifluoromethyl)pyridin-2-yl)benzamide (I-32);

4-methyl-3-((1-(1-(tetrahydro-2H-pyran-4-yl)-1H-pyrazol-4-yl)-1H-benzo[d]imidazol-5-yl)ethynyl)-N-(4-(trifluoromethyl)pyridin-2-yl)benzamide (I-33);

4-methyl-3-((1-(1-(1-methylpiperidin-4-yl)-1H-imidazol-4-yl)-1H-benzo[d]imidazol-5-yl)ethynyl)-N-(4-(trifluoromethyl)pyridin-2-yl)benzamide (I-34);

3-((1-(1H-pyrazol-4-yl)-1H-benzo[d]imidazol-5-yl)ethynyl)-4-methyl-N-(4-(trifluoromethyl)pyridin-2-yl)benzamide (I-35);

N-(4-methyl-3-((1-(1-methyl-1H-1,2,3-triazol-4-yl)-1H-benzo[d]imidazol-5-yl)ethynyl)phenyl)-4-(trifluoromethyl)picolinamide (I-36);

N-(4-cyano-3-(trifluoromethyl)phenyl)-4-methyl-3-((1-(1-methyl-1H-pyrazol-3-yl)-1H-benzo[d]imidazol-5-yl)ethynyl)benzamide (I-37);

N-(3-((1-(1-(2-methoxyethyl)-1H-pyrazol-4-yl)-1H-benzo[d]imidazol-5-yl)ethynyl)-4-methylphenyl)-4-(trifluoromethyl)picolinamide (I-38);

N-(3-((1-(1-(2-hydroxyethyl)-1H-pyrazol-4-yl)-1H-benzo[d]imidazol-5-yl)ethynyl)-4-methylphenyl)-4-(trifluoromethyl)picolinamide (I-39);

N-(3-((1-(1-(2-hydroxyethyl)-1H-pyrazol-4-yl)-1H-benzo[d]imidazol-5-yl)ethynyl)-4-methylphenyl)-4-(trifluoromethyl)picolinamide (I-40);

N-(3-((1-(1-(2-(dimethylamino)ethyl)-1H-pyrazol-4-yl)-1H-benzo[d]imidazol-5-yl)ethynyl)-4-methylphenyl)-4-(trifluoromethyl)picolinamide (I-41);

N-(3-((1-(1-(2-(diethylamino)ethyl)-1H-pyrazol-4-yl)-1H-benzo[d]imidazol-5-yl)ethynyl)-4-methylphenyl)-4-(trifluoromethyl)picolinamide (I-42);

N-(3-((1-(1H-pyrazol-4-yl)-1H-benzo[d]imidazol-5-yl)ethynyl)-4-methylphenyl)-4-(trifluoromethyl)picolinamide (I-43);

N-(4-methyl-3-((1-(1-methyl-1H-pyrazol-4-yl)-1H-benzo[d]imidazol-5-yl)ethynyl)phenyl)-4-(trifluoromethyl)picolinamide (I-44);

N-(4-methyl-3-((1-methyl-1H-benzo[d]imidazol-5-yl)ethynyl)phenyl)-4-(trifluoromethyl)picolinamide (I-45);

N-(4-methyl-3-((1-(1-methyl-1H-pyrazol-4-yl)-1H-benzo[d]imidazol-5-yl)ethynyl)phenyl)-4-((4-methylpiperazin-1-yl)methyl)-3-(trifluoromethyl)benzamide (I-46);

N-(4-methyl-3-((1-(1-methyl-1H-pyrazol-4-yl)-1H-benzo[d]imidazol-5-yl)ethynyl)phenyl)-4-(pyrrolidin-1-ylmethyl)-3-(trifluoromethyl)benzamide (I-47);

N-(4-methyl-3-((1-(1-methyl-1H-pyrazol-4-yl)-1H-benzo[d]imidazol-5-yl)ethynyl)phenyl)-4-(morpholinomethyl)-3-(trifluoromethyl)benzamide (I-48);

N-(3-((1-(1-methyl-1H-pyrazol-4-yl)-1H-benzo[d]imidazol-5-yl)ethynyl)phenyl)-4-(trifluoromethyl)picolinamide (I-49);

3-((1-(1-methyl-1H-pyrazol-4-yl)-1H-benzo[d]imidazol-5-yl)ethynyl)-N-(4-(trifluoromethyl)pyridin-2-yl)benzamide (I-50);

4-fluoro-3-((1-(1-methyl-1H-pyrazol-4-yl)-1H-benzo[d]imidazol-5-yl)ethynyl)-N-(4-(trifluoromethyl)pyridin-2-yl)benzamide); (I-51); and N-(4-fluoro-3-((1-(1-methyl-1H-pyrazol-4-yl)-1H-benzo[d]imidazol-5-yl)ethynyl)phenyl)-4-(trifluoromethyl)picolinamide (I-52).

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula (I) may form salts which are also within the scope of this invention. Reference to a compound of the Formula herein is understood to include reference to salts thereof, unless otherwise indicated.

The present invention relates to compounds which are modulators of c-Kit. In one embodiment, the compounds of the present invention are inhibitors of c-Kit.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Starting materials are either commercially available or made by known procedures in the reported literature or as illustrated. Compounds of the present invention can be synthesized by following the steps outlined in General Schemes 1 and 2 which comprise the assembling of intermediates 2a-2j and 3a-2c. Starting materials are either commercially available or made by known procedures in the reported literature or as illustrated.

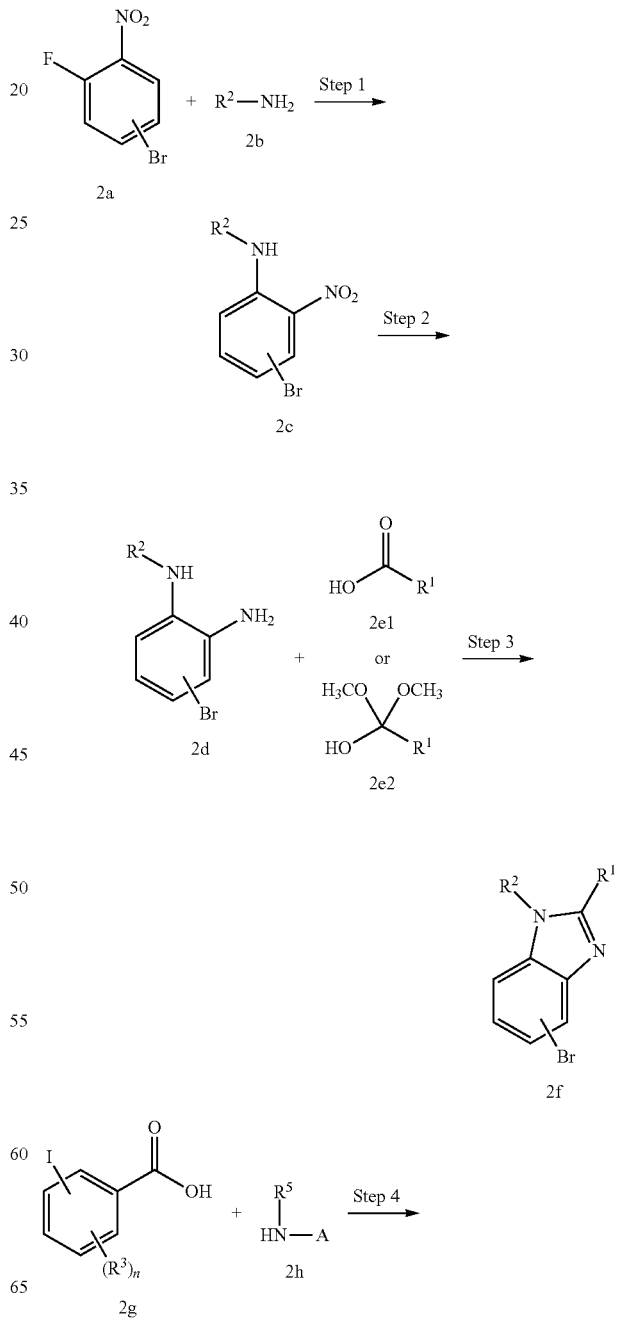

General Scheme 1

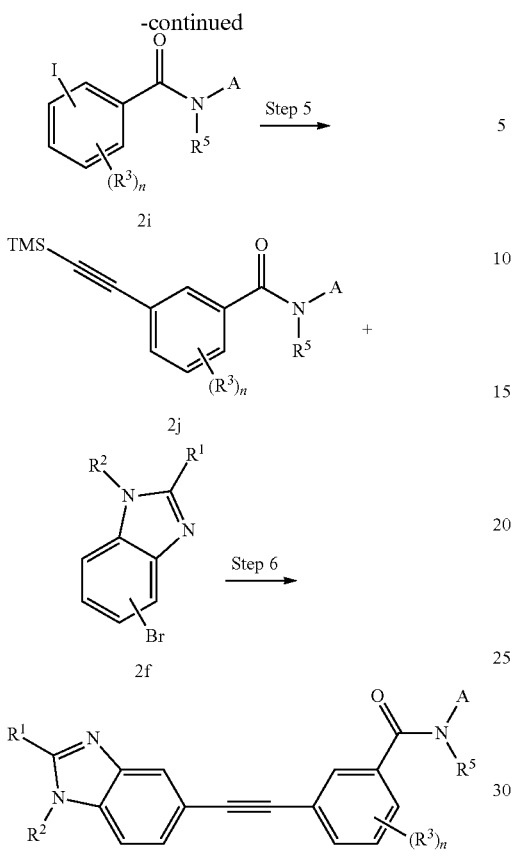

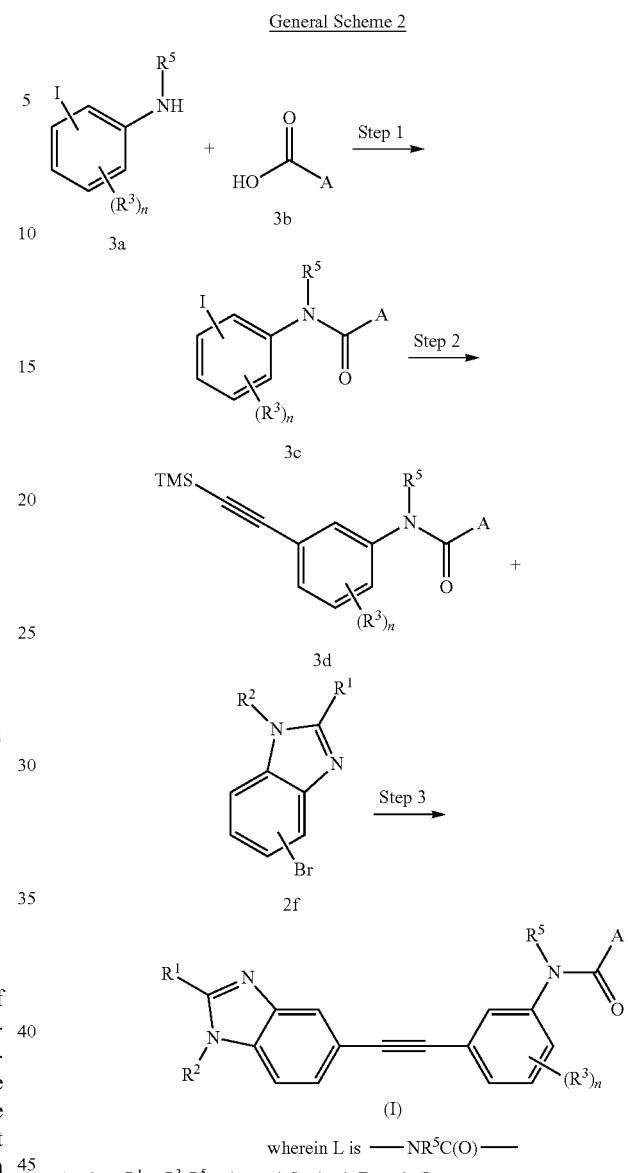

The general manner of preparing target compounds of Formula (I) wherein L is —C(O)NR$^5$— by using intermediates 2a-2j is outlined above in General Scheme 1. Nucleophilic addition of amine 2b to 2a in the presence of a base (i.e., potassium carbonate ($K_2CO_3$) or sodium carbonate ($Na_2CO_3$)) and in a solvent (i.e., acetonitrile (ACN)) at elevated temperatures provides intermediate 2c. Reduction of intermediate 2c in the presence of a metal (i.e., zinc), ammonium chloride ($NH_4Cl$), and a solvent (i.e., acetone/water) optionally at elevated temperature provides intermediate 2d. Cyclization of intermediate 2d with 2e2 optionally in a solvent (i.e., isopropanol) optionally at elevated temperature provides intermediate 2f. Alternatively, intermediate 2f can be obtained in one step from intermediates 2c and 2e1 using a metal (i.e., iron), ammonium chloride ($NH_4Cl$), and a solvent (i.e., isopropanol) at elevated temperatures. Intermediate 2i is obtained by treating intermediate 2g with thionyl chloride optionally in the presence of a solvent to form the acid chloride followed by acylation of amine 2h with the formed acid chloride using a base (i.e., N,N-diisopropyl ethyl amine (i-Pr$_2$NEt)) and 4-dimethylaminopyridine (DMAP) and optionally in a solvent (i.e., dichloromethane ($CH_2Cl_2$)). Coupling of alkyne 2j with bromide 2f in the presence of tetrakis(triphenylphosphine)palladium (0) (Pd(PPh$_3$)$_4$), copper iodide, a base (i.e., i-Pr$_2$NEt), optionally and in a solvent (i.e., ACN) optionally at elevated temperature provides the desired compounds of Formula (I) wherein L is —C(O)NR$^5$—.

The general manner of preparing target compounds of Formula (I) wherein L is —NR$^5$C(O)— by using intermediates 2e and 3a-3d is outlined above in General Scheme 2. Intermediate 3c is obtained by treating intermediate 3b with thionyl chloride optionally in the presence of a solvent to form the acid chloride followed by acylation of amine 3a with the formed acid chloride using a base (i.e., N,N-diisopropylethylamine (i-Pr$_2$NEt)) and 4-dimethylaminopyridine (DMAP) and optionally in a solvent (i.e., dichloromethane ($CH_2Cl_2$)). Coupling of alkyne 3d with bromide 2f in the presence of tetrakis(triphenylphosphine)palladium (0) (Pd(PPh$_3$)$_4$), copper iodide, a base (i.e., i-Pr$_2$NEt), optionally and in a solvent (i.e., ACN) optionally at elevated temperature provides the desired compounds of Formula (I) wherein L is —NR$^5$C(O)—.

Compounds of Formula (I) can exist as enantiomeric or diastereomeric stereoisomers. Enantiomerically pure compounds of Formula (I) can be prepared using enantiomerically pure chiral building blocks. Alternatively, racemic mixtures of the final compounds or a racemic mixture of an advanced intermediate can be subjected to chiral purification as described herein below to deliver the desired enantiomerically pure intermediates or final compounds. In the instances where an advanced intermediate is purified into its individual enantiomers, each individual enantiomer can be carried on separately to deliver the final enantiomerically pure compounds of Formula (I).

It should be understood that in the description and formula shown above, the various groups $R^1$-$R^5$, $R^{6a}$, $R^{6b}$, $R^7$-$R^9$, L, A, n, p, and q and other variables are as defined above, except where otherwise indicated. Furthermore, for synthetic purposes, the compounds of General Schemes 1 and 2 are merely representative with elected radicals to illustrate the general synthetic methodology of the compounds of Formula (I) as defined herein.

Methods of Using the Disclosed Compounds

Another aspect of the invention relates to a method of treating a disease or disorder associated with modulation of c-Kit. The method comprises administering to a patient in need of a treatment for a disease or disorder associated with modulation of c-Kit an effective amount the compositions and compounds of Formula (I).

Another aspect of the invention relates to a method of preventing a disease or disorder associated with modulation of c-Kit. The method comprises administering to a patient in need of a treatment for a disease or disorder associated with modulation of c-Kit an effective amount the compositions and compounds of Formula (I).

Another aspect of the invention relates to a method of treating a c-Kit-mediated disease or disorder. The method comprises administering to a patient in need of a treatment of a disease or disorder associated with modulation of c-Kit an effective amount the compositions and compounds of Formula (I).

Another aspect of the invention relates to a method of preventing a c-Kit-mediated disease or disorder. The method comprises administering to a patient in need of a treatment for diseases or disorders associated with modulation of c-Kit an effective amount the compositions and compounds of Formula (I).

In another aspect, the present invention is directed to a method of inhibiting c-Kit. The method involves administering to a patient in need thereof an effective amount of a compound of Formula (I).

Another aspect of the present invention relates to a method of treating a disease or disorder in a patient associated with the inhibition of c-Kit, the method comprising administering to a patient in need thereof an effective amount of a compound of Formula (I). In one embodiment, the disease or disorder is selected from the group consisting of cancer and cell proliferative disorders, multiple sclerosis, asthma, mastocytosis, inflammatory disorders, allergic reactions, fibrotic disorders, and metabolic disorders.

Another aspect of the present invention relates to a method of preventing a disease or disorder in a patient associated with the inhibition of c-Kit, the method comprising administering to a patient in need thereof an effective amount of a compound of Formula (I).

The present invention also relates to the use of an inhibitor of c-Kit for the preparation of a medicament used in the treatment, prevention, inhibition or elimination of a disease or disorder mediated by c-Kit, wherein the medicament comprises a compound of Formula (I).

In another aspect, the present invention relates to a method for the manufacture of a medicament for treating, preventing, inhibiting, or eliminating a disease or disorder mediated by c-Kit, wherein the medicament comprises a compound of Formula (I).

Another aspect of the present invention relates to a compound of Formula (I) for use in the manufacture of a medicament for treating a disease or disorder associated with inhibiting c-Kit.

In another aspect, the present invention relates to the use of a compound of Formula (I) in the treatment of a disease or disorder associated with inhibiting c-Kit.

In another aspect, the present invention relates to the use of a compound of Formula (I) in the prevention of a disease or disorder associated with inhibiting c-Kit.

In some embodiments of the methods above, the disease or disorder is selected from the group consisting of cancer, metastasis, inflammation and auto-immune pathogenesis.

In some embodiments of the methods above, the disease or disorder is selected from the group consisting of cell proliferative disorder, a fibrotic disorder, and a metabolic disorder.

In an embodiment of the methods above, the disease or disorder is multiple sclerosis.

In an embodiment of the methods above, the disease or disorder is asthma. In another embodiment of the methods above, the disease or disorder is mastocytosis.

In an embodiment of the methods above, the disease or disorder is an allergic reaction.

In an embodiment of the methods above, the disease or disorder is inflammatory arthritis.

Another aspect of the invention relates to a method of treating cancer. The method comprises administering to a patient in need thereof an effective amount of a compound of Formula (I).

In some embodiments, the cancer is selected from liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma.

In some embodiments, the cancer is selected from leukemia, mast cell tumor, small cell lung cancer, testicular cancer, cancer of the gastrointestinal tract, cancer of the central nervous system, cancer of the female genital tract, sarcoma of neuroectodermal origin, and Schwann cell neoplasia associated with neurofibromatosis.

In some embodiments, the cancer is selected from small cell lung carcinoma, acute myeloid leukemia (AML), thymic carcinoma, desmoid tumor, neuroblastoma, malignant melanomas, colorectal cancer, systemic mastocytosis (SM), and gastrointestinal stromal tumors (GISTs).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of c-Kit for the preparation of a medicament used in treatment, prevention, inhibition or elimination of a disease or disorder associated with associated with cancer and metastasis.

In some embodiments, administration of a compound of Formula (I) or a pharmaceutical composition comprising a compound of the present invention and a pharmaceutically acceptable carrier induces a change in the cell cycle or cell viability.

Another aspect of the invention relates to a method of treating inflammation. The method comprises administering to a patient in need thereof an effective amount of a compound of Formula (I).

Another aspect of the invention relates to a method of treating auto-immune pathogenesis. The method comprises administering to a patient in need thereof an effective amount of a compound of Formula (I).

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of c-Kit including, cancer and cell proliferative disorders, multiple sclerosis, asthma, inflammatory disorders, allergic reactions, fibrotic disorders, and metabolic disorders, comprising administering to a patient suffering from at least one of said diseases or disorder a compound of Formula (I).

In one embodiment, are provided methods of treating a disease or disorder associated with modulation of c-Kit including, cancer and metastasis, comprising administering to a patient suffering from at least one of said diseases or disorder a compound of Formula (I).

One therapeutic use of the compounds or compositions of the present invention which inhibit c-Kit is to provide treatment to patients or subjects suffering from cancer and cell proliferative disorders, multiple sclerosis, asthma, inflammatory disorders, allergic reactions, fibrotic disorders, and metabolic disorders.

Another therapeutic use of the compounds or compositions of the present invention which inhibit c-Kit is to provide treatment to patients or subjects suffering from cancer and metastasis.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on Bruker spectrometers at 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 μm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins.

Abbreviations used in the following examples and elsewhere herein are:
ACN acetonitrile
br broad
DCM dichloromethane
DIPEA N,N-diisopropyl ethyl amine
DMF N,N-dimethylformamide
DMSO dimethyl sulfoxide
EI electron ionization
ESI electrospray ionization
$Et_2O$ diethylether
EtOAc ethyl acetate
GCMS gas chromatography-mass spectrometry
h hour(s)
HPLC high-performance liquid chromatography
LCMS liquid chromatography-mass spectrometry
m multiplet
MeCN acetonitrile
MeOH methanol
MHz megahertz
min minutes
NMR nuclear magnetic resonance
$Pd(PPh_3)_4$ tetrakis(triphenylphosphine)palladium(0)
ppm parts per million
PSI Pounds per square inch
s singlet
TBAF tetra-n-butylammonium fluoride
v volume
wt weight General Method A for the Synthesis of Compounds of Formula (I)

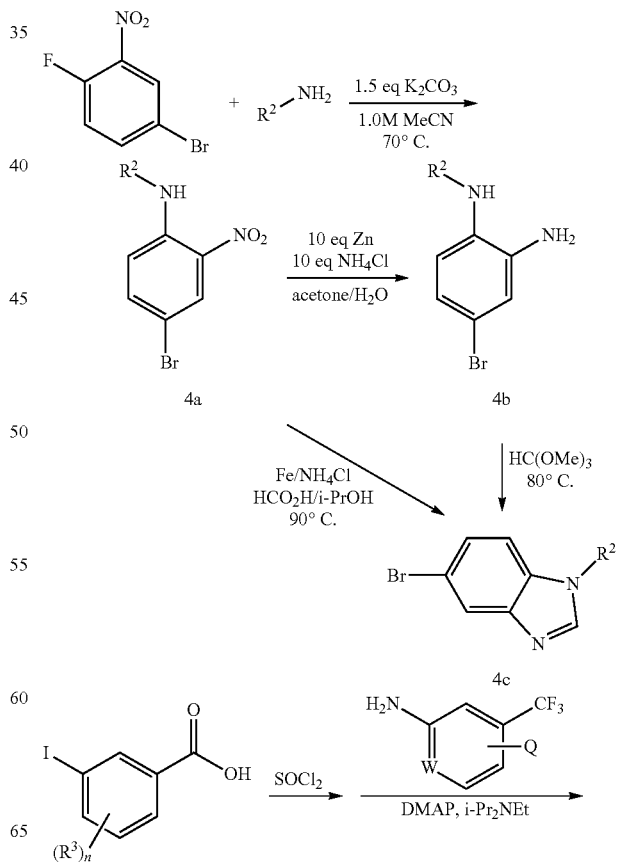

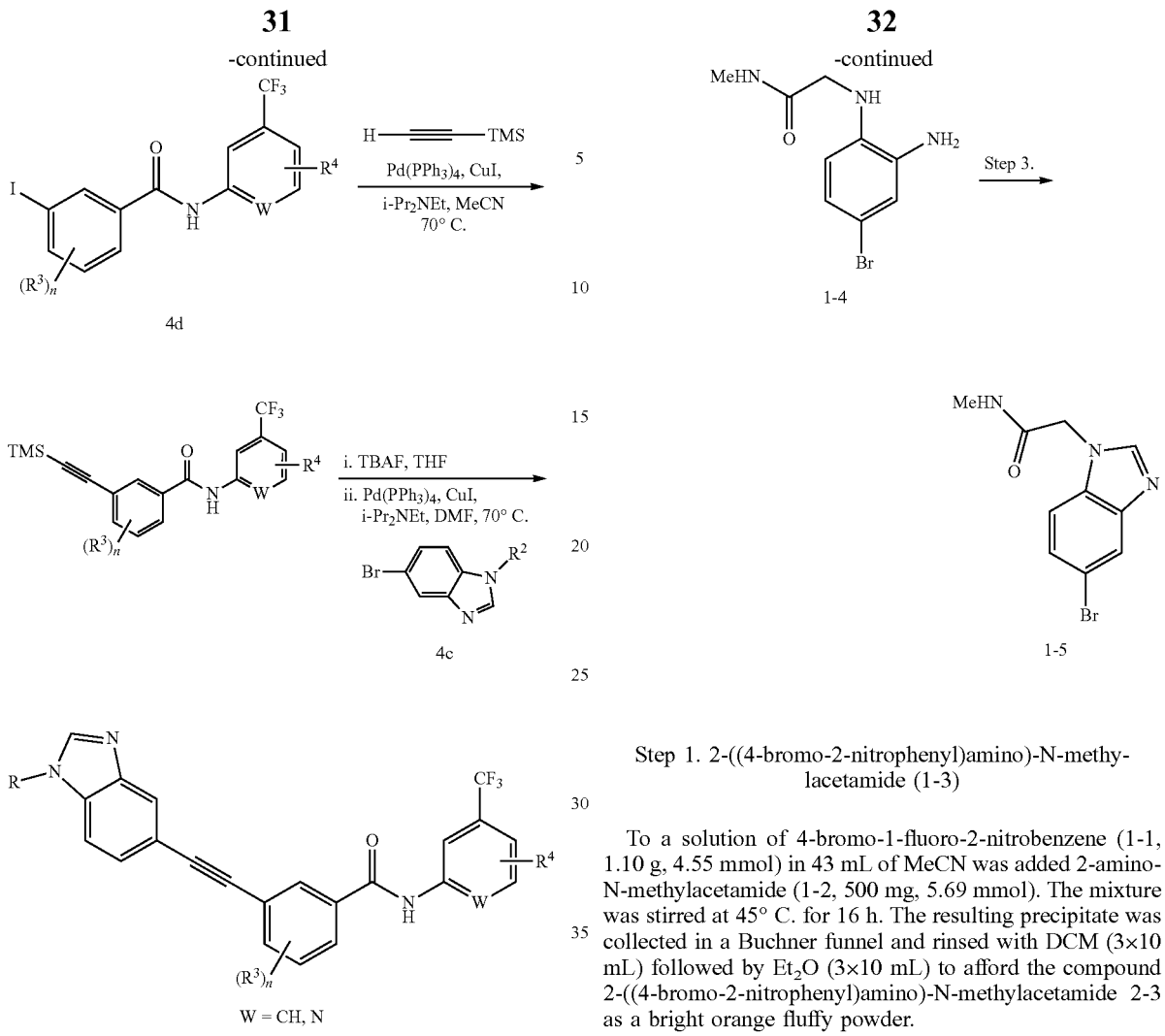

Example 1: 2-(5-Bromo-1H-benzo[d]imidazol-1-yl)-N-methylacetamide (Intermediate 1-5)

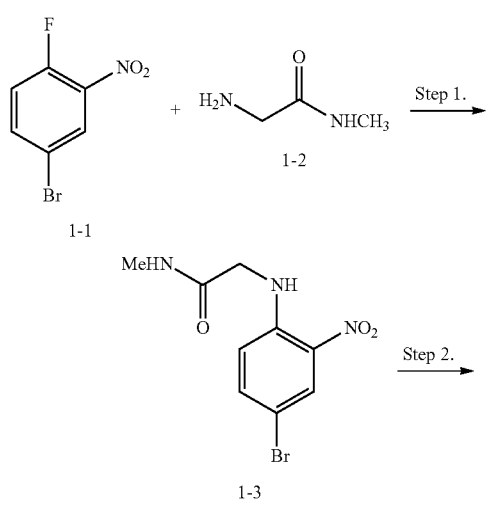

Step 1. 2-((4-bromo-2-nitrophenyl)amino)-N-methylacetamide (1-3)

To a solution of 4-bromo-1-fluoro-2-nitrobenzene (1-1, 1.10 g, 4.55 mmol) in 43 mL of MeCN was added 2-amino-N-methylacetamide (1-2, 500 mg, 5.69 mmol). The mixture was stirred at 45° C. for 16 h. The resulting precipitate was collected in a Buchner funnel and rinsed with DCM (3×10 mL) followed by Et$_2$O (3×10 mL) to afford the compound 2-((4-bromo-2-nitrophenyl)amino)-N-methylacetamide 2-3 as a bright orange fluffy powder.

Step 2. 2-((2-amino-4-bromophenyl)amino)-N-methylacetamide (1-4)

After stirring a mixture of 2-((4-bromo-2-nitrophenyl)amino)-N-methylacetamide (1-3, 932 mg, 3.23 mmol) and zinc (0) (1.68 g, 25.84 mmol) in acetone for approximately 1 min, a pre-mixed solution of NH$_4$Cl (2.57 g, 48.45 mmol) in water was added and the resulting mixture was stirred for 1 h at rt to give a colorless solution and then concentrated in vacuo. The crude residue was extracted with DCM (3×100 mL), and the combined organic layers were dried over sodium sulfate, filtered through Celite, and concentrated in vacuo to afford the compound 2-((2-amino-4-bromophenyl)amino)-N-methylacetamide 1-4.

Step 3. 2-(5-bromo-1H-benzo[d]imidazol-1-yl)-N-methylacetamide (1-5)

2-((2-Amino-4-bromophenyl)amino)-N-methylacetamide (1-4, 300 mg, 1.16 mmol) and trimethylorthoformate (12 mL) were combined and stirred for 24 h at 80° C. under an atmosphere of argon. The resulting mixture was concentrated in vacuo to give a brown solid. The solid was washed with Et$_2$O (3×10 mL) to afford the compound 2-(5-bromo-1H-benzo[d]imidazol-1-yl)-N-methylacetamide 1-5 as a brown powder.

Example 2: 5-Bromo-1-(1-methyl-1H-pyrazol-4-yl)-1H-benzo[d]imidazole (Intermediate 2-2)

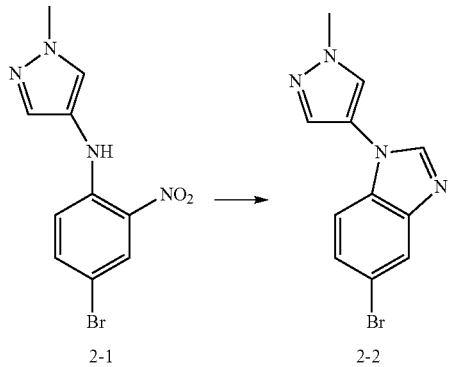 [SMILES: Cn1cc(Nc2ccc(Br)cc2[N+](=O)[O-])cn1 ; Cn1cc(-n2cnc3cc(Br)ccc32)cn1]

N-(4-Bromo-2-nitrophenyl)-1-methyl-1H-pyrazol-4-amine (2-1, 6.85 g, 23.14 mmol) was combined with iron (Fe) (12.9 g, 231.14 mmol), ammonium chloride (12.9 g, 231.14 mmol), 20 mL of formic acid (HCOOH) and 20 mL of isopropanol. The mixture was stirred at 90° C. for 16 h. The solid was filtered through celite and the filtrate was concentrated under reduced pressure. The crude residue was purified by flash chromatography on silica gel eluting with 0 to 15% MeOH/EtOAc to afford 5.1 g of 5-bromo-1-(1-methyl-1H-pyrazol-4-yl)-1H-benzo[d]imidazole 2-2 as a grey solid.

Example 3: 4-Methyl-3-((1-(2-(methylamino)-2-oxoethyl)-1H-benzo[d]imidazol-5-yl)ethynyl)-N-(4-(trifluoromethyl)pyridin-2-yl)benzamide (I-1)

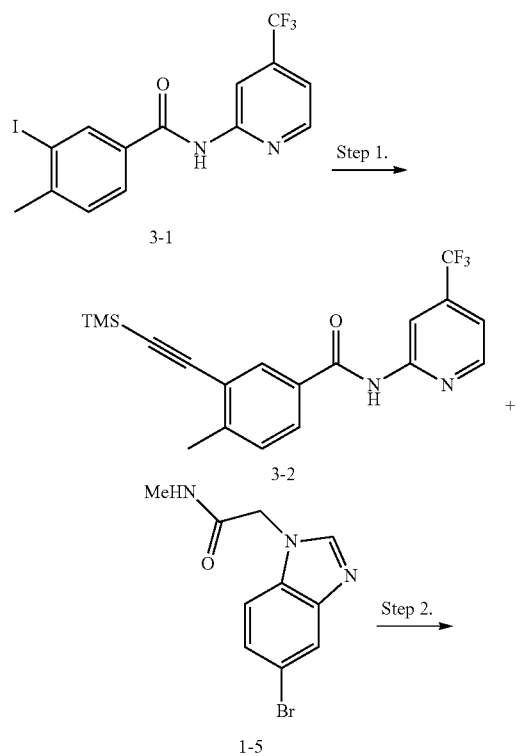

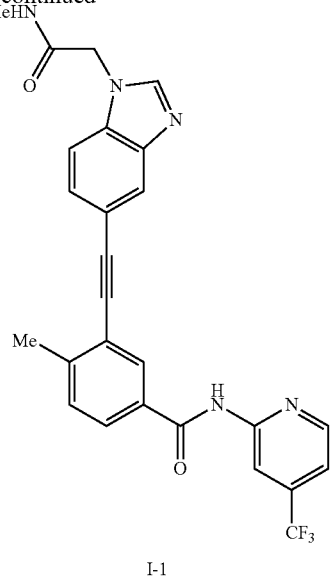

Step 1. 4-Methyl-N-(4-(trifluoromethyl)pyridin-2-yl)-3((trimethylsilyl)ethynyl)benzamide (3-2)

3-Iodo-4-methyl-N-(4-(trifluoromethyl)pyridin-2-yl)benzamide (3-1, 5 g, 12.3 mmol) was combined with Pd(PPh$_3$)$_4$ (430 mg, 0.37 mmol) and CuI (120 mg, 0.63 mmol) in a schlenk flask. The flask was placed under an inert atmosphere by evacuating and was back filling the schlenk flask with N$_2$. DIPEA (4.3 mL, 24.6 mmol), ethynyltrimethylsilane (3.5 mL, 24.6 mmol) and 25 mL of MeCN were then added. The resulting mixture was then stirred at 85° C. for 3 h, cooled to rt and concentrated under reduced pressure. The crude residue was purified by flash chromatography on silica gel with 0 to 10% EtOAc/heptane to afford 4.47 g of 4-methyl-N-(4-(trifluoromethyl)pyridin-2-yl)-3-((trimethylsilyl)ethynyl)benzamide 3-2 as a brown solid.

Step 2. 4-Methyl-3-((1-(2-(methylamino)-2-oxoethyl)-1H-benzo[d]imidazol-5-yl)ethynyl)-N-(4-(trifluoromethyl)pyridin-2-yl)benzamide (I-1)

4-Methyl-N-(4-(trifluoromethyl)pyridin-2-yl)-3-((trimethylsilyl)ethynyl)benzamide (3-2, 150 mg, 0.40 mmol) was added to a solution of TBAF (0.42 mL, 0.40 mmol) in 2 mL of THF in a microwave vial and the resulting brown solution was stirred for 10 min at rt. The reaction mixture was concentrated using a nitrogen stream to give an oil. 2-(5-Bromo-1H-benzo[d]imidazol-1-yl)-N-methylacetamide (1-5, 71 mg, 0.27 mmol), Pd(PPh$_3$)$_4$ (9 mg, 0.0078 mmol), 1 mL iPr$_2$NH, and 4 mL DMF were then added to the vial and the mixture was stirred for 1 min. CuI (3 mg, 0.016 mmol) was added and the vial was purged with argon and then heated to 100° C. for 45 min in a microwave oven. After cooling to rt, the reaction mixture was concentrated in vacuo and purified by flash column chromatography on silica gel (eluting with 0% to 15% MeOH/EtOAc) to afford the title compound as a brown powder (I-1). 71% yield. $^1$H-NMR (DMSO-d$_6$) δ: 11.31 (s, 1H), 8.70 (d, J=5.0 Hz, 1H), 8.55 (s, 1H), 8.16-8.30 (m, 3H), 7.96 (dd, J=7.9, 2.0 Hz, 1H), 7.91 (d, J=0.6 Hz, 1H), 7.53-7.58 (m, 2H), 7.46-7.52 (m, 2H), 4.97 (s, 2H), 2.66 (d, J=4.5 Hz, 3H), 2.59 (s, 3H). ESI-MS m/z: 492.1 [M+H]$^+$.

The following compounds in Table 1 were prepared in analogous fashion to Example 3. The bromide intermediates 4c were either purchased from commercial sources, or synthesized as described in Examples 1 or 2. The intermediate 4d or its reverse amide analogs were made by standard amide formation method as described in *J. Med. Chem.* 2009, 52, 4743 and *J. Med. Chem.* 2010, 53, 4701. For Compound 1-26, the starting aniline used was tert-butyl 4-(4-amino-1H-pyrazol-1-yl)piperidine-1-carboxylate A shown herein below. For Compound 1-35 and Compound 1-43, the starting aniline used was 1-tosyl-1H-pyrazol-4-amine B shown herein below.

TABLE 1

| Cmpd No. | Compound Structure | $^1$H NMR (400 MHz) δ (ppm): | ESI-MS m/z [M + H]$^+$ |
|---|---|---|---|
| I-2 | 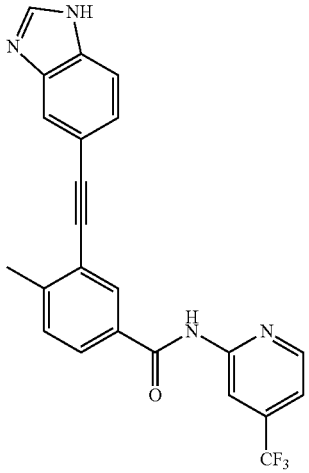 [SMILES: Cc1ccc(C(=O)Nc2cc(C(F)(F)F)ccn2)cc1C#Cc1ccc2[nH]cnc2c1] | | 421.1 |
| I-3 | 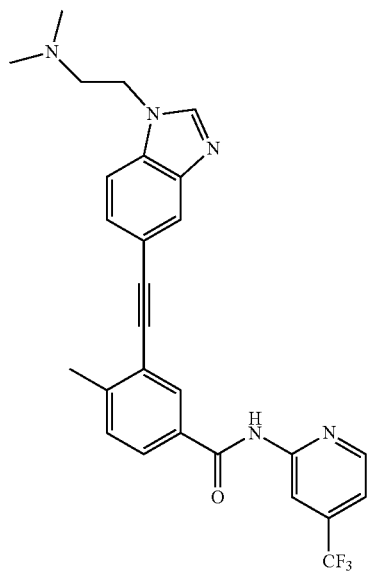 [SMILES: Cc1ccc(C(=O)Nc2cc(C(F)(F)F)ccn2)cc1C#Cc1ccc2c(c1)ncn2CCN(C)C] | (DMSO-d$_6$): δ 11.31 (s, 1H), 8.70 (d, J = 5.1 Hz, 1H), 8.55 (s, 1H), 8.33 (s, 1H), 8.24 (d, J = 2.0 Hz, 1H), 7.97 (dd, J = 7.9, 1.9 Hz, 1H), 7.90 (d, J = 0.9 Hz, 1H), 7.72 (d, J = 7.9 Hz, 1H), 7.43-7.59 (m, 3H), 4.37 (t, J = 6.3 Hz, 2H), 2.62-2.72 (m, 2H), 2.59 (s, 3H), 2.20 (s, 6H) | 492.2 |

TABLE 1-continued
| Cmpd No. | Compound Structure | $^1$H NMR (400 MHz) δ (ppm): | ESI-MS m/z [M + H]$^+$ |
|---|---|---|---|
| I-4 | 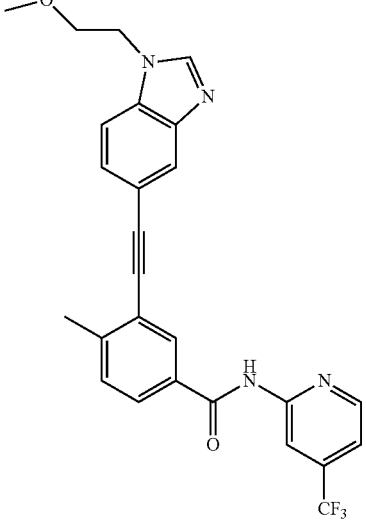 [SMILES: COCCn1cnc2cc(C#Cc3cc(C(=O)Nc4cc(C(F)(F)F)ccn4)ccc3C)ccc21] | (DMSO-d$_6$): δ 11.31 (s, 1H), 8.70 (d, J = 5.1 Hz, 1H), 8.55 (s, 1H), 8.29 (s, 1H), 8.24 (d, J = 2.0 Hz, 1H), 7.97 (dd, J = 8.0, 1.9 Hz, 1H), 7.90 (d, J = 0.8 Hz, 1H), 7.72 (d, J = 7.9 Hz, 1H), 7.46-7.59 (m, 3H), 4.46 (s, 2H), 3.71 (t, J = 5.1 Hz, 2H), 3.25 (s, 3H), 2.59 (s, 3H) | 479.1 |
| I-5 | 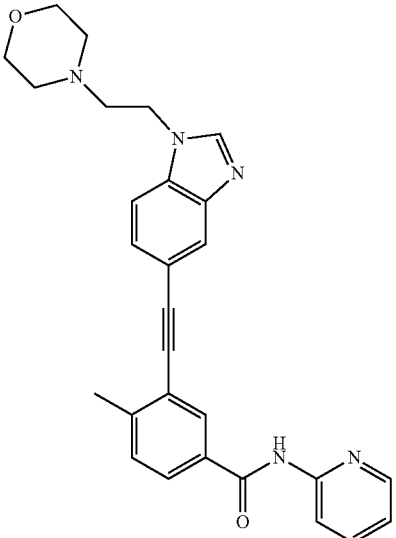 | (DMSO-d$_6$): δ 11.31 (s, 1H), 8.70 (d, J = 5.1 Hz, 1H), 8.55 (s, 1H), 8.36 (br. s., 1H), 8.24 (d, J = 2.0 Hz, 1H), 7.97 (dd, J = 8.0, 1.9 Hz, 1H), 7.90 (s, 1H), 7.73 (d, J = 8.4 Hz, 1H), 7.55 (dd, J = 5.0, 1.0 Hz, 1H), 7.46-7.53 (m, 2H), 4.40 (t, J = 6.1 Hz, 2H), 3.47-3.61 (m, 4H), 2.71 (t, J = 6.1 Hz, 2H), 2.59 (s, 3H), 2.41-2.48 (m, 4H) | 534.2 |

TABLE 1-continued

| Cmpd No. | Compound Structure | $^1$H NMR (400 MHz) δ (ppm): | ESI-MS m/z [M + H]$^+$ |
|---|---|---|---|
| I-6 | 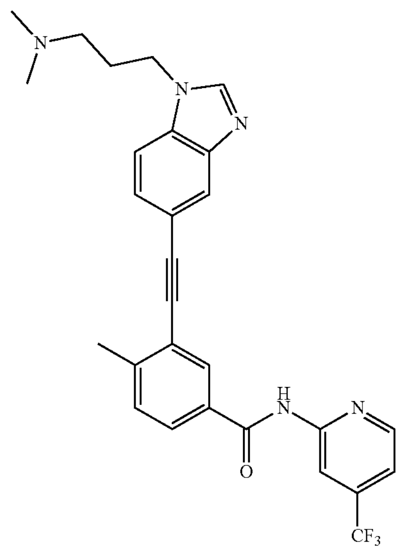 [SMILES: Cc1ccc(C(=O)Nc2cc(C(F)(F)F)ccn2)cc1C#Cc1ccc2c(c1)ncn2CCCN(C)C] | (DMSO-d$_6$): δ 11.31 (s, 1H), 8.69 (d, J = 5.1 Hz, 1H), 8.55 (s, 1H), 8.33 (s, 1H), 8.24 (d, J = 2.0 Hz, 1H), 7.97 (dd, J = 8.0, 1.9 Hz, 1H), 7.91 (d, J = 0.9 Hz, 1H), 7.70 (d, J = 8.4 Hz, 1H), 7.46-7.59 (m, 3H), 4.31 (t, J = 7.0 Hz, 2H), 2.59 (s, 3H), 2.11-2.21 (m, 8H), 1.95 (t, J = 6.9 Hz, 2H) | 506.2 |
| I-7 | 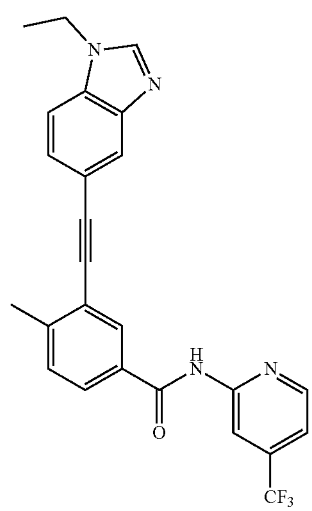 [SMILES: CCn1cnc2cc(C#Cc3cc(C(=O)Nc4cc(C(F)(F)F)ccn4)ccc3C)ccc21] | (DMSO-d$_6$): δ 11.31 (s, 1H), 8.70 (d, J = 5.1 Hz, 1H), 8.55 (s, 1H), 8.38 (s, 1H), 8.25 (d, J = 1.9 Hz, 1H), 7.97 (dd, J = 8.0, 1.9 Hz, 1H), 7.91 (s, 1H), 7.72 (d, J = 8.3 Hz, 1H), 7.55 (dd, J = 5.1, 1.0 Hz, 1H), 7.50 (d, J = 8.4 Hz, 2H), 4.32 (q, J = 7.3 Hz, 2H), 2.59 (s, 3H), 1.44 (t, J = 7.3 Hz, 3H) | 449.1 |

TABLE 1-continued

| Cmpd No. | Compound Structure | $^1$H NMR (400 MHz) δ (ppm): | ESI-MS m/z [M + H]$^+$ |
|---|---|---|---|
| I-8 | 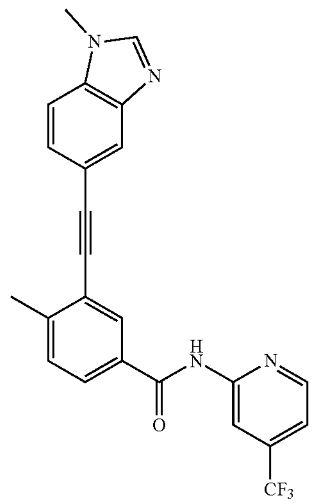 | (DMSO-d$_6$): δ 11.31 (s, 1H), 8.70 (d, J = 5.0 Hz, 1H), 8.55 (s, 1H), 8.31 (br. s., 1H), 8.25 (d, J = 1.9 Hz, 1H), 7.87-8.01 (m, 2H), 7.64-7.70 (m, 1H), 7.51 (s, 3H), 3.89 (s, 3H), 2.59 (s, 3H) | 435.1 |
| I-10 | 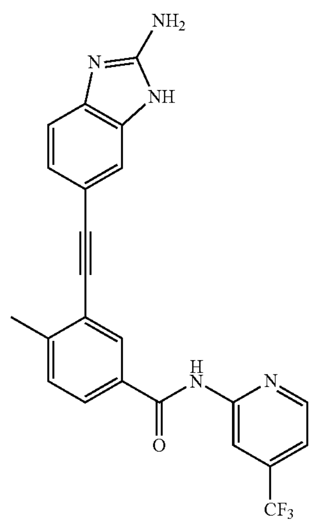 [SMILES: Cc1ccc(C(=O)Nc2cc(C(F)(F)F)ccn2)cc1C#Cc1ccc2nc(N)[nH]c2c1] | (DMSO-d$_6$): δ 11.28 (s, 1H), 10.92 (br. s., 1H), 8.69 (d, J = 5.1 Hz, 1H), 8.54 (d, J = 0.8 Hz, 1H), 8.19 (d, J = 2.0 Hz, 1H), 7.93 (dd, J = 8.0, 1.9 Hz, 1H), 7.54 (dd, J = 5.1, 1.0 Hz, 1H), 7.47 (d, J = 8.0 Hz, 1H), 7.32 (s, 1H), 7.14 (s, 2H), 6.40 (br. s., 2H), 2.55 (s, 3H) | |
| I-11 | 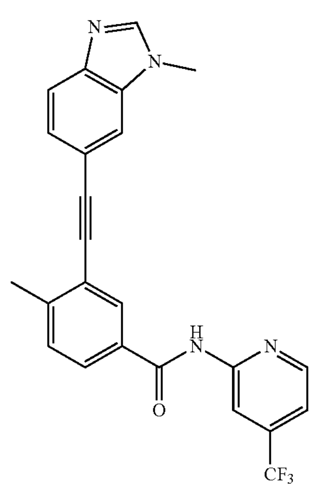 [SMILES: Cc1ccc(C(=O)Nc2cc(C(F)(F)F)ccn2)cc1C#Cc1ccc2ncn(C)c2c1] | (DMSO-d$_6$): δ 11.32 (s, 1H), 8.70 (d, J = 5.1 Hz, 1H), 8.55 (s, 1H), 8.21-8.36 (m, 2H), 7.98 (dd, J = 8.0, 1.9 Hz, 1H), 7.89 (d, J = 1.0 Hz, 1H), 7.71 (d, J = 8.4 Hz, 1H), 7.48-7.58 (m, 2H), 7.44 (dd, J = 8.3, 1.5 Hz, 1H), 3.89 (s, 3H), 2.60 (s, 3H) | |

TABLE 1-continued
| Cmpd No. | Compound Structure | ¹H NMR (400 MHz) δ (ppm): | ESI-MS m/z [M + H]⁺ |
|---|---|---|---|
| I-12 | 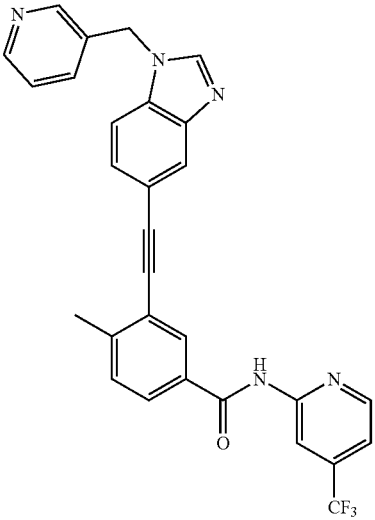 [SMILES: Cc1ccc(C(=O)Nc2cc(C(F)(F)F)ccn2)cc1C#Cc1ccc2c(c1)ncn2Cc1cccnc1] | (DMSO-d₆): δ 11.30 (s, 1H), 8.69 (d, J = 5.1 Hz, 2H), 8.47-8.60 (m, 3H), 8.23 (d, J = 2.0 Hz, 1H), 7.87-8.03 (m, 2H), 7.71 (dd, J = 16.1, 8.2 Hz, 2H), 7.55 (dd, J = 5.2, 0.9 Hz, 1H), 7.55-7.52 (m, 2H), 7.39 (dd, J = 7.8, 4.8 Hz, 1H), 5.61 (s, 2H), 2.57 (s, 3H) | |
| I-13 | 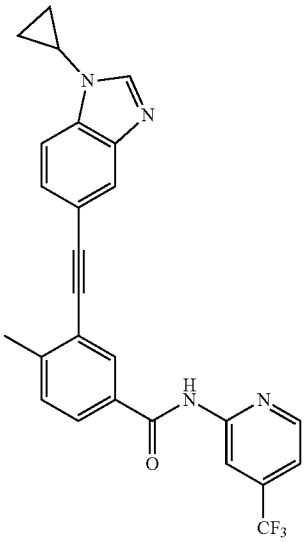 [SMILES: Cc1ccc(C(=O)Nc2cc(C(F)(F)F)ccn2)cc1C#Cc1ccc2c(c1)ncn2C1CC1] | (DMSO-d₆): δ 11.31 (s, 1H), 8.70 (d, J = 5.1 Hz, 1H), 8.55 (s, 1H), 8.34 (s, 1H), 8.25 (d, J = 1.9 Hz, 1H), 7.97 (dd, J = 8.0, 1.9 Hz, 1H), 7.91 (s, 1H), 7.71 (d, J = 8.3 Hz, 1H), 7.45-7.59 (m, 3H), 3.56 (dt, J = 7.2, 3.4 Hz, 1H), 2.59 (s, 3H), 1.03-1.17 (m, 4H) | |

TABLE 1-continued

| Cmpd No. | Compound Structure | $^1$H NMR (400 MHz) δ (ppm): | ESI-MS m/z [M + H]$^+$ |
|---|---|---|---|
| I-14 | 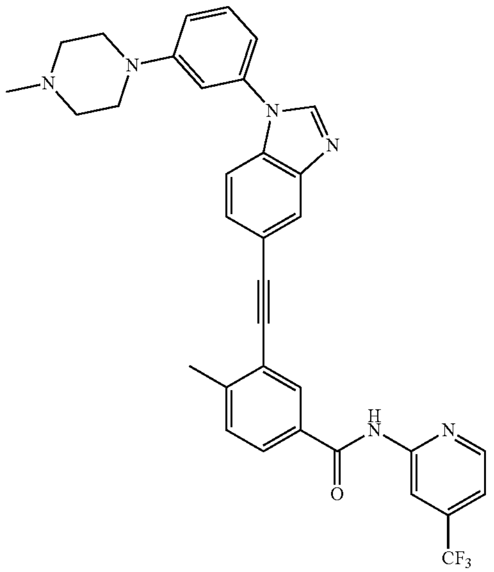 [SMILES: Cc1ccc(C(=O)Nc2cc(C(F)(F)F)ccn2)cc1C#Cc1ccc2c(c1)ncn2-c1cccc(N2CCN(C)CC2)c1] | (DMSO-d$_6$): δ 11.32 (s, 1H), 8.70 (d, J = 5.1 Hz, 1H), 8.66 (s, 1H), 8.55 (d, J = 0.8 Hz, 1H), 8.26 (d, J = 1.9 Hz, 1H), 8.02-8.05 (m, 1H), 7.96-8.01 (m, 1H), 7.69 (d, J = 8.4 Hz, 1H), 7.45-7.61 (m, 4H), 7.24 (s, 1H), 7.09-7.17 (m, 2H), 3.37-3.55 (m, 2H), 2.81-3.21 (m, 4H), 2.60 (m, 5H) | 595.2 |
| I-15 | 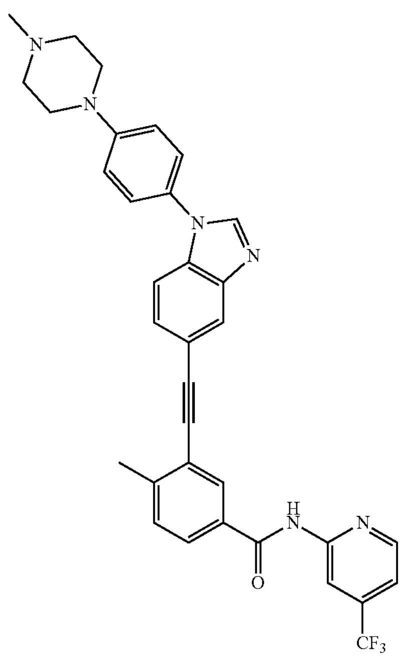 [SMILES: Cc1ccc(C(=O)Nc2cc(C(F)(F)F)ccn2)cc1C#Cc1ccc2c(c1)ncn2-c1ccc(N2CCN(C)CC2)cc1] | (DMSO-d$_6$): δ 11.31 (s, 1H), 8.70 (d, J = 5.1 Hz, 1H), 8.55 (s, 2H), 8.26 (d, J = 1.9 Hz, 1H), 7.93-8.05 (m, 2H), 7.49-7.62 (m, 6H), 7.17 (d, J = 9.2 Hz, 2H), 3.24-3.29 (m, 4H), 2.60 (s, 3H), 2.27 (s, 3H) | 595.2 |

TABLE 1-continued

| Cmpd No. | Compound Structure | $^1$H NMR (400 MHz) δ (ppm): | ESI-MS m/z [M + H]$^+$ |
|---|---|---|---|
| I-17 | 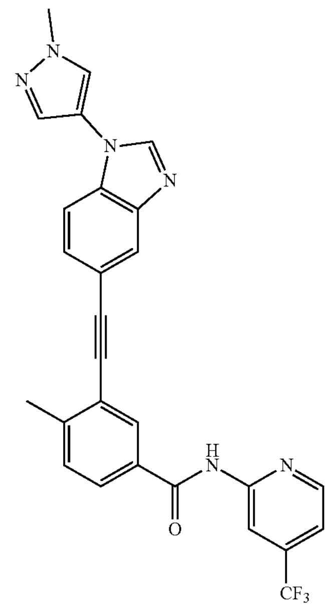 [SMILES: Cc1ccc(C(=O)Nc2cc(C(F)(F)F)ccn2)cc1C#Cc1ccc2c(c1)ncn2-c1cnn(C)c1] | (DMSO-d$_6$): δ 10.52 (s, 1H), 8.30 (s, 1H), 8.22 (d, J = 1.8 Hz, 1H), 8.18 (d, J = 1.9 Hz, 1H), 8.10 (d, J = 8.7 Hz, 1H), 7.88-7.94 (m, 2H), 7.72 (d, J = 8.5 Hz, 1H), 7.67 (d, J = 7.9 Hz, 1H), 7.49-7.55 (m, 2H), 3.88 (s, 3H), 3.51 (br. s., 2H), 2.59 (s, 3H), 2.20 (s, 6H) | 491.2 |
| I-18 | 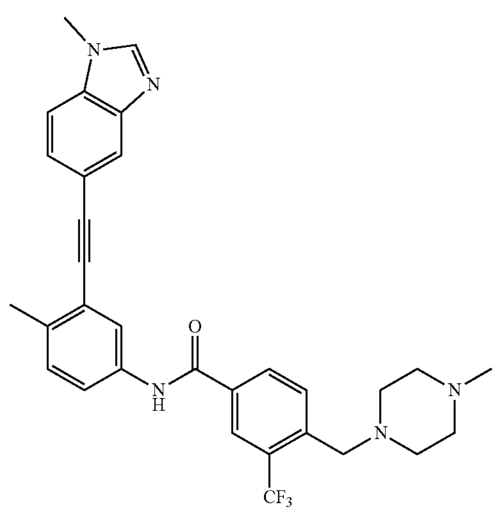 | (DMSO-d$_6$): δ 10.53 (s, 1H), 8.30 (s, 1H), 8.20 (dd, J = 19.6, 1.9 Hz, 2H), 8.06-8.13 (m, 1H), 7.88-7.96 (m, 2H), 7.64-7.77 (m, 2H), 7.52 (dt, J = 8.3, 1.5 Hz, 2H), 3.88 (s, 3H), 3.61 (s, 2H), 2.59 (s, 3H), 2.37 (br. s., 4H) | 546.2 |

TABLE 1-continued

| Cmpd No. | Compound Structure | ¹H NMR (400 MHz) δ (ppm): | ESI-MS m/z [M + H]⁺ |
|---|---|---|---|
| I-19 | 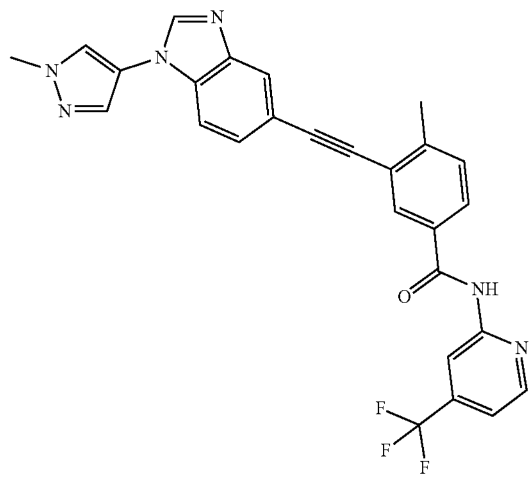 [SMILES: Cc1ccc(C(=O)Nc2cc(C(F)(F)F)ccn2)cc1C#Cc1ccc2c(c1)ncn2-c1cnn(C)c1] | (DMSO-d$_6$): δ 11.31 (s, 1H), 8.70 (d, J = 5.1 Hz, 1H), 8.55 (s, 2H), 8.39 (s, 1H), 8.26 (d, J = 1.9 Hz, 1H), 7.94-8.05 (m, 3H), 7.63-7.71 (m, 1H), 7.48-7.60 (m, 3H), 3.96 (s, 3H), 2.60 (s, 3H) | 501.1 |
| I-20 | 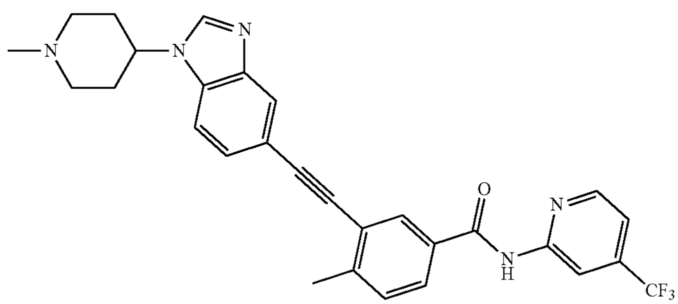 [SMILES: Cc1ccc(C(=O)Nc2cc(C(F)(F)F)ccn2)cc1C#Cc1ccc2c(c1)ncn2C1CCN(C)CC1] | (Chloroform-d): δ 8.73 (d, J = 4.3 Hz, 1H), 8.73 (s, 1H), 8.51 (d, J = 5.1 Hz, 1H), 8.03-8.12 (m, 3H), 7.83 (dd, J = 8.0, 2.0 Hz, 1H), 7.40-7.55 (m, 3H), 7.28 (s, 4H), 3.10 (d, J = 4.8 Hz, 2H), 2.65 (s, 3H), 2.42 (s, 3H), 2.16-2.31 (m, 6H), 1.62 (br. s., 7H) | 518.5 |
| I-21 | 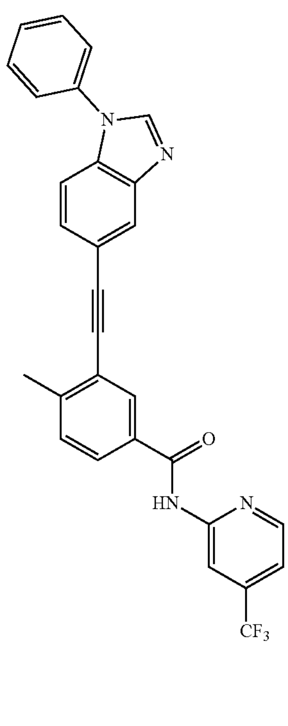 [SMILES: Cc1ccc(C(=O)Nc2cc(C(F)(F)F)ccn2)cc1C#Cc1ccc2c(c1)ncn2-c1ccccc1] | (Chloroform-d): δ 8.68-8.76 (m, 2H), 8.51 (d, J = 5.1 Hz, 1H), 8.20 (s, 1H), 8.10-8.14 (m, 2H), 7.84 (dd, J = 8.0, 2.0 Hz, 1H), 7.51-7.66 (m, 7H), 7.44 (d, J = 7.9 Hz, 1H), 7.28 (s, 5H), 2.67 (s, 3H), 1.59 (br. s., 3H) | 497.4 |

TABLE 1-continued

| Cmpd No. | Compound Structure | ¹H NMR (400 MHz) δ (ppm): | ESI-MS m/z [M + H]⁺ |
|---|---|---|---|
| I-22 | 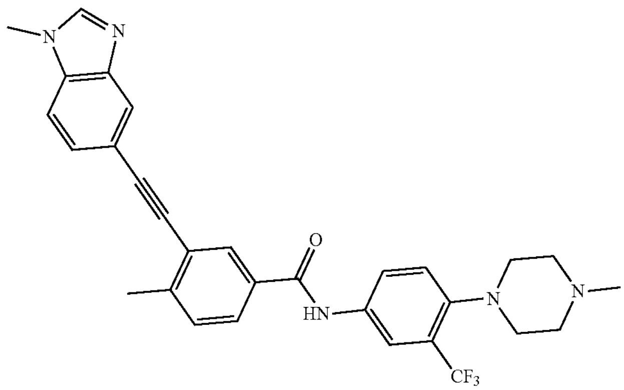 | | 532.2 |
| I-23 | 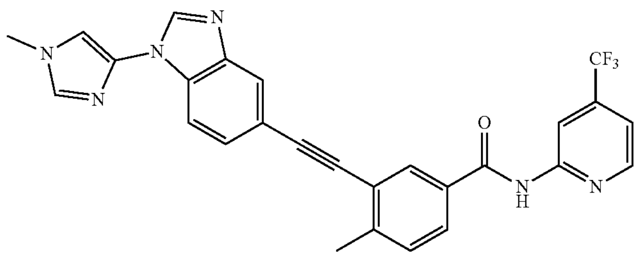 [SMILES: Cc1ccc(C(=O)Nc2cc(C(F)(F)F)ccn2)cc1C#Cc1ccc2c(c1)ncn2-c1cn(C)cn1] | (Chloroform-d): δ 8.80 (s, 1H), 8.70 (dt, J = 1.6, 0.9 Hz, 1H), 8.47 (dt, J = 5.2, 0.8 Hz, 1H), 8.35 (s, 1H), 8.15-7.98 (m, 2H), 7.80 (dd, J = 8.0, 2.0 Hz, 1H), 7.68 (d, J = 8.4 Hz, 1H), 7.53 (dd, J = 8.4, 1.4 Hz, 1H), 7.48 (d, J = 1.4 Hz, 1H), 7.43-7.36 (m, 1H), 7.29 (ddd, J = 5.1, 1.6, 0.7 Hz, 1H), 7.09 (d, J = 1.5 Hz, 1H), 3.81 (s, 3H), 2.63 (s, 3H). | 501.1 |
| I-24 | 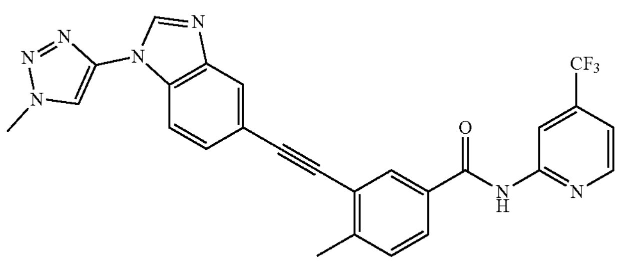 [SMILES: Cc1ccc(C(=O)Nc2cc(C(F)(F)F)ccn2)cc1C#Cc1ccc2c(c1)ncn2-c1cn(C)nn1] | (DMSO-d₆): δ 11.31 (s, 1H), 8.77 (s, 1H), 8.73 (s, 1H), 8.71-8.65 (m, 1H), 8.54 (dt, J = 1.6, 0.8 Hz, 1H), 8.26 (d, J = 2.0 Hz, 1H), 8.04 (dd, J = 1.6, 0.7 Hz, 1H), 7.95 (ddd, J = 16.2, 8.2, 1.4 Hz, 2H), 7.63 (dd, J = 8.4, 1.5 Hz, 1H), 7.58-7.46 (m, 2H), 4.20 (s, 3H), 2.59 (s, 3H) | 502.1 |
| I-25 | 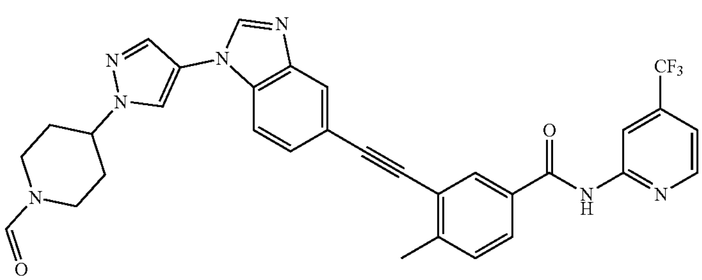 [SMILES: Cc1ccc(C(=O)Nc2cc(C(F)(F)F)ccn2)cc1C#Cc1ccc2c(c1)ncn2-c1cnn(C2CCN(C=O)CC2)c1] | (Chloroform-d): δ 8.71 (d, J = 8.5 Hz, 2H), 8.48 (d, J = 5.1 Hz, 1H), 8.17-7.99 (m, 4H), 7.87-7.71 (m, 3H), 7.53 (dd, J = 8.4, 1.5 Hz, 1H), 7.40 (t, J = 8.6 Hz, 2H), 7.30 (dd, J = 5.2, 1.5 Hz, 1H), 4.60 (d, J = 13.7 Hz, 1H), 4.49 (tt, J = 11.3, 4.0 Hz, 1H), 3.86 (d, J = 13.3 Hz, 1H), 3.41-3.25 (m, 1H), 2.90 (ddd, J = 13.6, 11.9, 3.2 Hz, 1H), 2.63 (s, 3H), 2.34 (dd, J = 27.1, 12.7 Hz, 2H), 2.03 (dqd, J = 18.7, 12.0, 4.7 Hz, 2H) | 598.2 |
| I-26 | 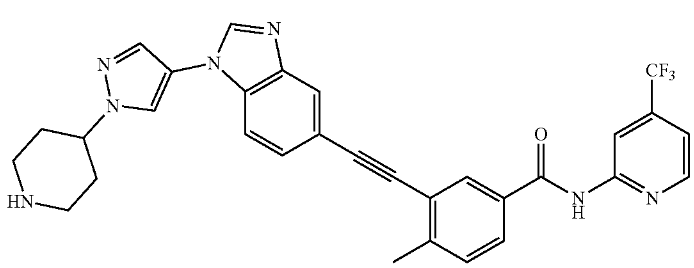 [SMILES: Cc1ccc(C(=O)Nc2cc(C(F)(F)F)ccn2)cc1C#Cc1ccc2c(c1)ncn2-c1cnn(C2CCNCC2)c1] | (Chloroform-d): δ 8.85 (s, 1H), 8.70 (p, J = 0.8 Hz, 1H), 8.47 (d, J = 5.1 Hz, 1H), 8.14-7.95 (m, 3H), 7.81 (dd, J = 8.0, 2.0 Hz, 1H), 7.78-7.69 (m, 2H), 7.52 (dd, J = 8.4, 1.5 Hz, 1H), 7.44-7.33 (m, 2H), 7.32-7.28 (m, 1H), 4.31 (tt, J = 11.7, 4.1 Hz, 1H), 3.29 (d, J = 12.5 Hz, 2H), 2.95-2.73 (m, 2H), 2.63 (s, 3H), 2.25 (d, J = 11.6 Hz, 2H), 1.98 (td, J = 12.2, 4.0 Hz, 2H), 1.70 (s, 1H) | 570.4 |

TABLE 1-continued

| Cmpd No. | Compound Structure | ¹H NMR (400 MHz) δ (ppm): | ESI-MS m/z [M + H]⁺ |
|---|---|---|---|
| I-27 | 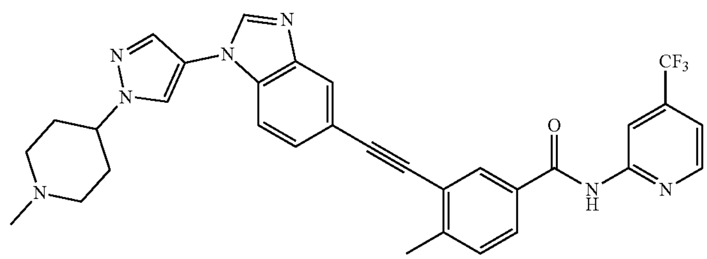 [SMILES: Cc1ccc(C(=O)Nc2cc(C(F)(F)F)ccn2)cc1C#Cc1ccc2c(c1)ncn2-c1cnn(C2CCN(C)CC2)c1] | (Chloroform-d): δ 8.64-8.82 (m, 2H), 8.48 (d, J = 5.14 Hz, 1H), 7.98-8.15 (m, 3H), 7.69-7.87 (m, 3H), 7.52 (dd, J = 1.38, 8.41 Hz, 1H), 7.39 (t, J = 7.53 Hz, 2H), 7.27-7.33 (m, 1H), 4.06-4.34 (m, 1H), 2.98-3.11 (m, 2H), 2.63 (s, 3H), 2.36 (s, 3H), 2.08-2.30 (m, 6H) | 584.4 |
| I-28 | 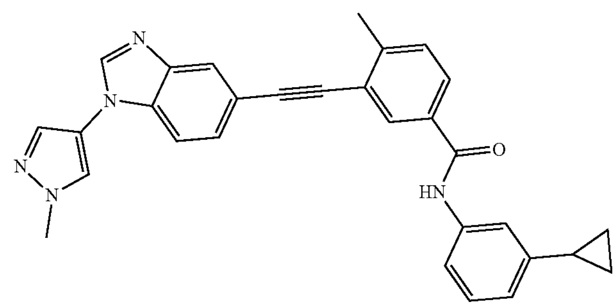 [SMILES: Cc1ccc(C(=O)Nc2cccc(C3CC3)c2)cc1C#Cc1ccc2c(c1)ncn2-c1cnn(C)c1] | (Methanol-d₄): δ 9.12 (s, 1H), 8.30-8.22 (m, 1H), 8.11 (d, J = 2.0 Hz, 1H), 8.02 (dd, J = 1.3, 0.8 Hz, 1H), 7.96 (d, J = 0.8 Hz, 1H), 7.86 (dd, J = 8.0, 2.0 Hz, 1H), 7.73 (dd, J = 3.4, 1.1 Hz, 2H), 7.50-7.42 (m, 3H), 7.27-7.19 (m, 1H), 6.95-6.86 (m, 1H), 4.05 (s, 3H), 2.63 (s, 3H), 1.94 (tt, J = 8.4, 5.1 Hz, 1H), 1.05-0.94 (m, 2H), 0.76-0.65 (m, 2H) | 472.1 |
| I-29 | 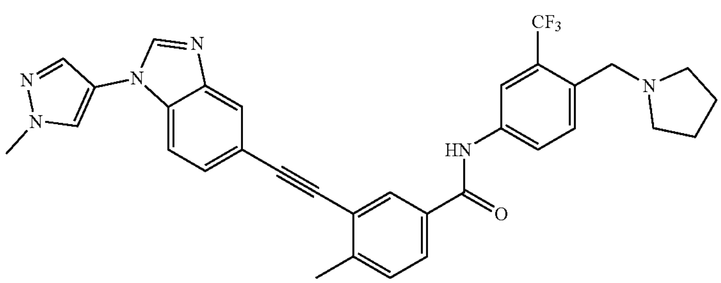 [SMILES: Cc1ccc(C(=O)Nc2ccc(CN3CCCC3)c(C(F)(F)F)c2)cc1C#Cc1ccc2c(c1)ncn2-c1cnn(C)c1] | (Chloroform-d): δ 8.37 (s, 1H), 8.05 (s, 1H), 8.03-7.96 (m, 3H), 7.91 (dd, J = 8.5, 2.3 Hz, 1H), 7.84 (d, J = 8.6 Hz, 1H), 7.77 (dd, J = 7.9, 2.0 Hz, 1H), 7.73 (dd, J = 9.3, 0.8 Hz, 2H), 7.49 (dd, J = 8.4, 1.4 Hz, 1H), 7.39-7.31 (m, 2H), 4.04 (s, 3H), 3.83 (s, 2H), 2.63 (d, J = 5.9 Hz, 4H), 2.60 (s, 3H), 1.89-1.79 (m, 4H) | 583.2 |
| I-30 | 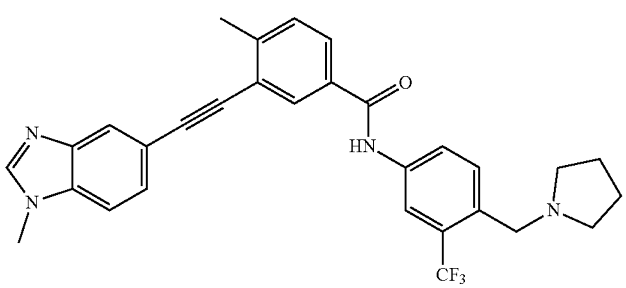 [SMILES: Cc1ccc(C(=O)Nc2ccc(CN3CCCC3)c(C(F)(F)F)c2)cc1C#Cc1ccc2c(c1)ncn2C] | (Chloroform-d): δ 8.30 (s, 1H), 8.07 (d, J = 21.7 Hz, 2H), 8.01-7.96 (m, 2H), 7.94 (dd, J = 8.4, 2.2 Hz, 1H), 7.85 (d, J = 8.5 Hz, 1H), 7.74 (dd, J = 8.0, 2.0 Hz, 1H), 7.51 (d, J = 8.3 Hz, 1H), 7.42 (d, J = 8.6 Hz, 1H), 7.31 (d, J = 8.1 Hz, 1H), 3.89 (s, 3H), 3.84 (s, 2H), 2.63 (s, 4H), 2.58 (s, 3H) | 517.2 |
| I-31 | 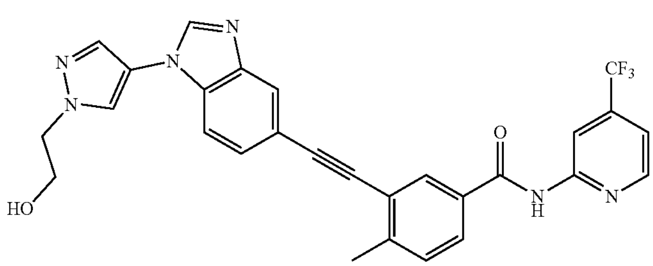 [SMILES: Cc1ccc(C(=O)Nc2cc(C(F)(F)F)ccn2)cc1C#Cc1ccc2c(c1)ncn2-c1cnn(CCO)c1] | (Chloroform-d): δ 8.73-8.66 (m, 2H), 8.49 (d, J = 5.2 Hz, 1H), 8.11-8.01 (m, 3H), 7.85-7.77 (m, 3H), 7.54 (dd, J = 8.4, 1.5 Hz, 1H), 7.41 (dt, J = 8.4, 0.9 Hz, 2H), 7.33-7.25 (m, 1H), 4.41-4.34 (m, 2H), 4.13 (q, J = 5.4 Hz, 2H), 2.64 (s, 3H) | 531.3 |

TABLE 1-continued

| Cmpd No. | Compound Structure | ¹H NMR (400 MHz) δ (ppm): | ESI-MS m/z [M + H]⁺ |
|---|---|---|---|
| I-32 | 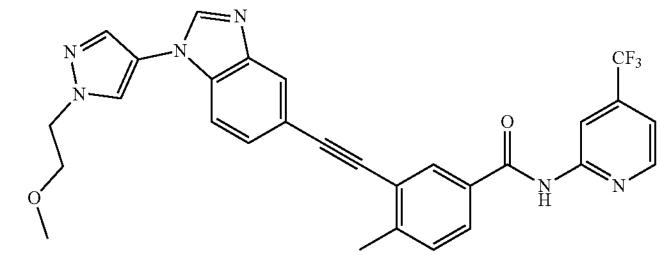 [SMILES: COCCn1cc(-n2cnc3cc(C#Cc4cc(C(=O)Nc5cc(C(F)(F)F)ccn5)ccc4C)ccc32)cn1] | (Chloroform-d): δ 8.75-8.67 (m, 2H), 8.48 (d, J = 5.1 Hz, 1H), 8.07 (d, J = 2.2 Hz, 3H), 7.86-7.74 (m, 3H), 7.53 (dd, J = 8.4, 1.2 Hz, 1H), 7.41 (dd, J = 8.2, 6.4 Hz, 2H), 7.33-7.24 (m, 1H), 4.44-4.36 (m, 2H), 3.86-3.79 (m, 2H), 3.40 (s, 3H), 2.63 (s, 3H) | 545.3 |
| I-33 | 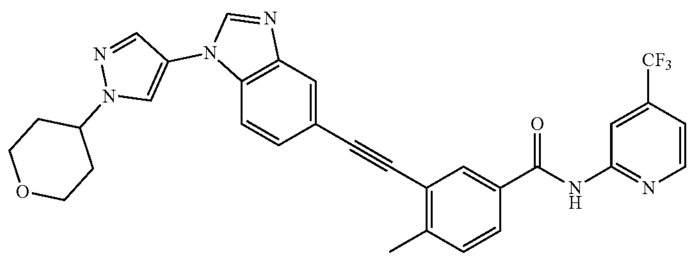 [SMILES: Cc1ccc(C(=O)Nc2cc(C(F)(F)F)ccn2)cc1C#Cc1ccc2c(c1)ncn2-c1cnn(C2CCOCC2)c1] | (Chloroform-d): δ 8.84 (s, 1H), 8.70 (dt, J = 1.5, 0.8 Hz, 1H), 8.47 (dt, J = 5.1, 0.8 Hz, 1H), 8.11-8.01 (m, 3H), 7.84-7.69 (m, 3H), 7.52 (dd, J = 8.4, 1.4 Hz, 1H), 7.39 (dd, J = 8.2, 2.1 Hz, 2H), 7.32-7.24 (m, 1H), 4.52-4.33 (m, 1H), 4.21-4.12 (m, 2H), 3.59 (td, J = 11.6, 2.7 Hz, 2H), 2.63 (s, 3H), 2.28-2.07 (m, 4H) | 571.4 |
| I-34 | 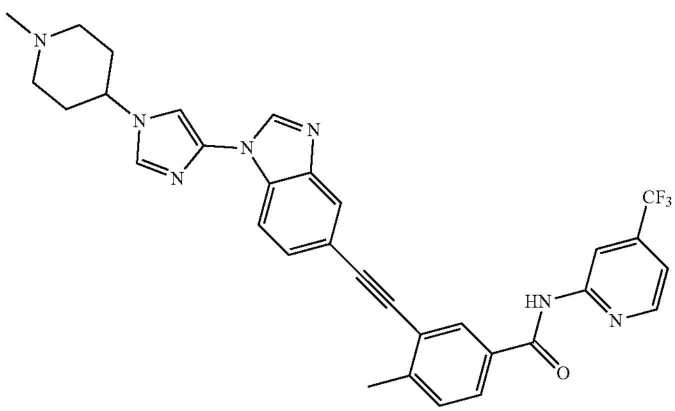 [SMILES: Cc1ccc(C(=O)Nc2cc(C(F)(F)F)ccn2)cc1C#Cc1ccc2c(c1)ncn2-c1cn(C2CCN(C)CC2)cn1] | (Chloroform-d): δ 8.65 (d, J = 11.9 Hz, 2H), 8.41 (d, J = 5.1 Hz, 1H), 8.28 (s, 1H), 8.04-7.96 (m, 2H), 7.74 (dd, J = 8.0, 2.1 Hz, 1H), 7.61 (d, J = 8.4 Hz, 1H), 7.55-7.43 (m, 2H), 7.34 (d, J = 8.2 Hz, 1H), 7.22 (t, J = 6.1 Hz, 1H), 7.10 (d, J = 1.6 Hz, 1H), 3.96 (s, 1H), 2.99 (d, J = 9.5 Hz, 2H), 2.57 (s, 3H), 2.31 (s, 3H), 2.13-1.93 (m, 6H) | 584.5 |
| I-35 | 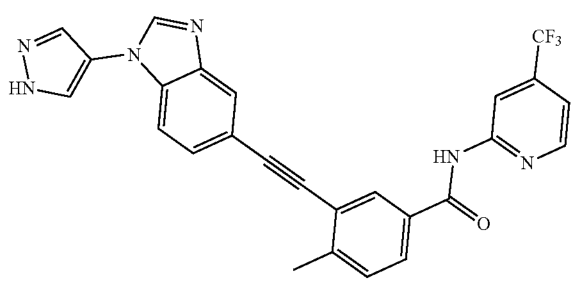 [SMILES: Cc1ccc(C(=O)Nc2cc(C(F)(F)F)ccn2)cc1C#Cc1ccc2c(c1)ncn2-c1cn[nH]c1] | (Chloroform-d): δ 11.52 (s, 1H), 9.74 (s, 1H), 8.82 (s, 1H), 8.55 (d, J = 5.2 Hz, 1H), 8.31 (d, J = 2.0 Hz, 1H), 8.05-7.96 (m, 4H), 7.89 (dd, J = 7.9, 2.1 Hz, 1H), 7.43-7.26 (m, 5H), 2.63 (s, 3H) | 487.1 |
| I-36 | 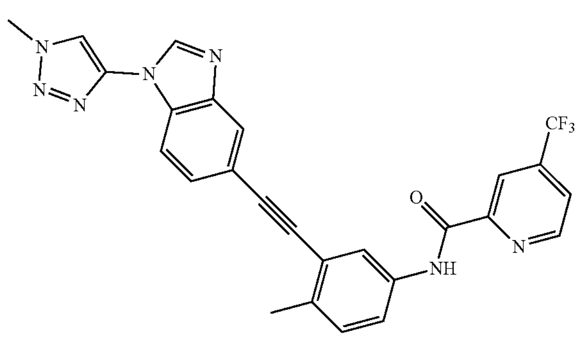 [SMILES: Cc1ccc(NC(=O)c2cc(C(F)(F)F)ccn2)cc1C#Cc1ccc2c(c1)ncn2-c1cn(C)nn1] | (Chloroform-d): δ 9.88 (s, 1H), 8.82 (dt, J = 5.0, 0.7 Hz, 1H), 8.54 (dt, J = 1.7, 0.8 Hz, 1H), 8.38 (s, 1H), 8.06 (dd, J = 1.5, 0.7 Hz, 1H), 7.92 (d, J = 2.4 Hz, 1H), 7.83 (s, 1H), 7.75-7.64 (m, 3H), 7.57 (dd, J = 8.4, 1.4 Hz, 1H), 7.28 (d, J = 8.3 Hz, 1H), 4.25 (s, 3H), 2.55 (s, 3H) | 502.4 |

TABLE 1-continued

| Cmpd No. | Compound Structure | $^1$H NMR (400 MHz) δ (ppm): | ESI-MS m/z [M + H]$^+$ |
|---|---|---|---|
| I-37 | 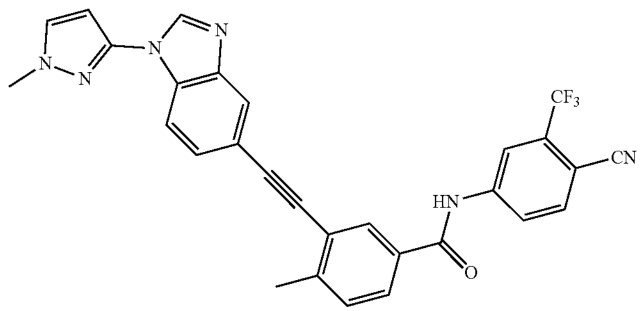 [SMILES: Cc1ccc(C(=O)Nc2ccc(C#N)c(C(F)(F)F)c2)cc1C#Cc1ccc2c(c1)ncn2-c1ccn(C)n1] | (Chloroform-d): δ 8.35 (s, 1H), 8.17-8.07 (m, 2H), 8.05-7.98 (m, 3H), 7.87-7.67 (m, 4H), 7.50 (dd, J = 8.4, 1.4 Hz, 1H), 7.39 (dd, J = 8.3, 2.2 Hz, 2H), 4.04 (s, 3H), 2.62 (s, 3H) | 525.3 |
| I-38 | 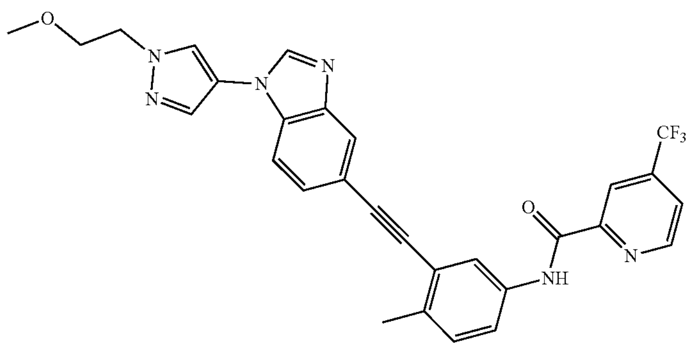 [SMILES: COCCn1cc(-n2cnc3cc(C#Cc4cc(NC(=O)c5cc(C(F)(F)F)ccn5)ccc4C)ccc32)cn1] | (Chloroform-d) δ 9.91 (s, 1H), 8.84 (d, J = 5.0 Hz, 1H), 8.58 (dd, J = 1.8, 0.9 Hz, 1H), 8.07 (dd, J = 1.4, 0.7 Hz, 1H), 8.06 (s, 1H), 7.94 (d, J = 2.4 Hz, 1H), 7.85 (d, J = 0.8 Hz, 1H), 7.81-7.70 (m, 3H), 7.55 (dd, J = 8.4, 1.5 Hz, 1H), 7.42 (dd, J = 8.4, 0.7 Hz, 1H), 7.34-7.27 (m, 1H), 4.42 (dd, J = 5.5, 4.6 Hz, 2H), 3.85 (dd, J = 5.5, 4.6 Hz, 2H), 3.43 (s, 3H), 2.58 (s, 3H) | 545.2 |
| I-39 | 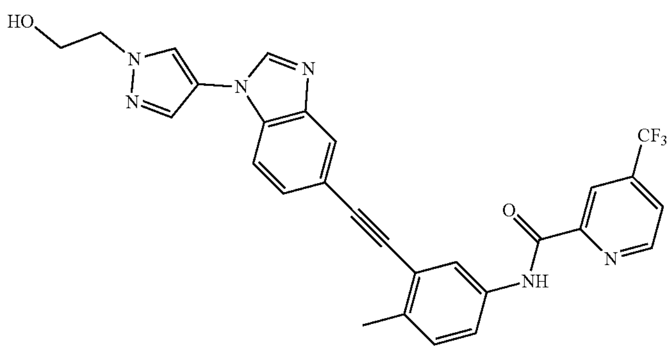 [SMILES: Cc1ccc(NC(=O)c2cc(C(F)(F)F)ccn2)cc1C#Cc1ccc2c(c1)ncn2-c1cnn(CCO)c1] | (Chloroform-d): δ 9.81 (s, 1H), 8.75 (dd, J = 4.9, 0.8 Hz, 1H), 8.48 (dt, J = 1.7, 0.8 Hz, 1H), 8.00-7.92 (m, 2H), 7.96-7.82 (m, 1H), 7.77-7.67 (m, 2H), 7.68-7.61 (m, 2H), 7.45 (dd, J = 8.4, 1.5 Hz, 1H), 7.32 (dd, J = 8.4, 0.7 Hz, 1H), 7.21 (d, J = 8.3 Hz, 1H), 4.34-4.24 (m, 2H), 4.10-4.03 (m, 2H), 2.48 (s, 3H), 1.95 (s, 1H) | 531.2 |
| I-40 | 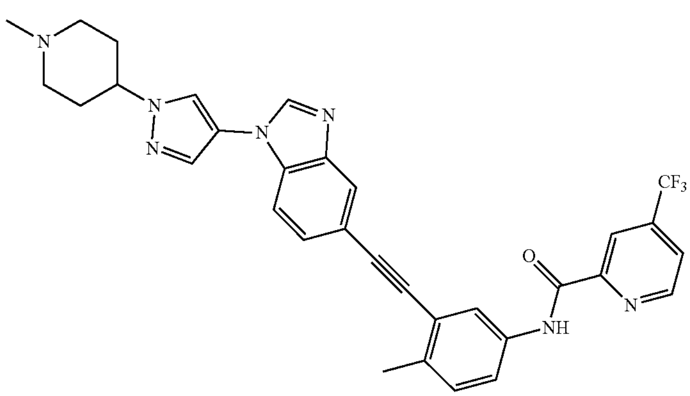 [SMILES: Cc1ccc(NC(=O)c2cc(C(F)(F)F)ccn2)cc1C#Cc1ccc2c(c1)ncn2-c1cnn(C2CCN(C)CC2)c1] | (Chloroform-d): δ 9.91 (s, 1H), 8.84 (dt, J = 5.0, 0.7 Hz, 1H), 8.57 (dt, J = 1.7, 0.8 Hz, 1H), 8.09-8.01 (m, 1H), 7.94 (d, J = 2.4 Hz, 1H), 7.81-7.71 (m, 4H), 7.54 (dd, J = 8.4, 1.4 Hz, 1H), 7.39 (dd, J = 8.3, 0.7 Hz, 1H), 7.30 (d, J = 8.2 Hz, 1H), 4.24 (s, 1H), 3.09-3.01 (m, 2H), 2.57 (s, 3H), 2.38 (s, 3H), 2.28 (dd, J = 7.1, 2.7 Hz, 1H), 2.26 (s, 1H), 2.27-2.07 (m, 3H) | 584.5 |

TABLE 1-continued

| Cmpd No. | Compound Structure | ¹H NMR (400 MHz) δ (ppm): | ESI-MS m/z [M + H]⁺ |
|---|---|---|---|
| I-41 | 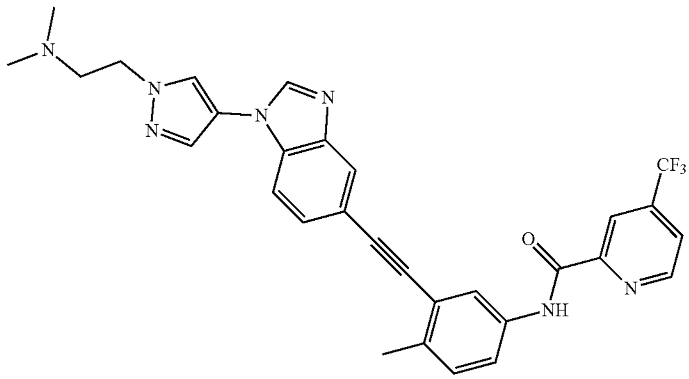 [SMILES: Cc1ccc(NC(=O)c2cc(C(F)(F)F)ccn2)cc1C#Cc1ccc2c(c1)ncn2-c1cnn(CCN(C)C)c1] | (Chloroform-d): δ 9.72 (s, 1H), 8.65 (dt, J = 5.0, 0.8 Hz, 1H), 8.38 (dt, J = 1.6, 0.8 Hz, 1H), 7.95-7.78 (m, 2H), 7.79-7.66 (m, 2H), 7.61-7.52 (m, 3H), 7.40-7.25 (m, 1H), 7.28-7.17 (m, 1H), 7.18-7.01 (m, 1H), 4.16 (dd, J = 7.3, 5.4 Hz, 2H), 2.67 (t, J = 6.3 Hz, 2H), 2.39 (s, 3H), 2.16 (s, 6H). | 558.2 |
| I-42 | 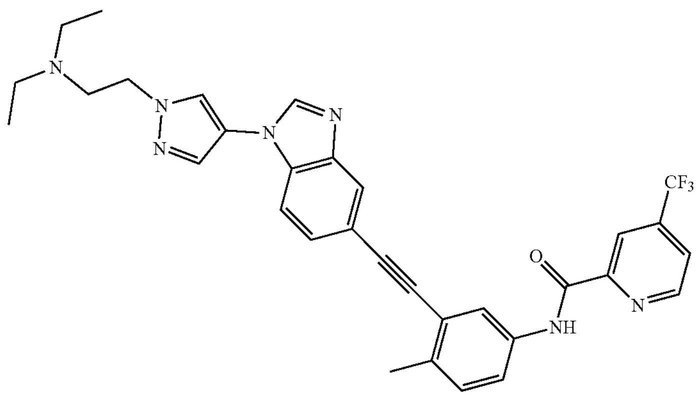 [SMILES: CCN(CC)CCn1cc(-n2cnc3cc(C#Cc4cc(NC(=O)c5cc(C(F)(F)F)ccn5)ccc4C)ccc32)cn1] | (Chloroform-d): δ 9.72 (s, 1H), 8.64 (dt, J = 5.0, 0.8 Hz, 1H), 8.37 (dt, J = 1.6, 0.8 Hz, 1H), 7.92-7.79 (m, 2H), 7.82-7.70 (m, 1H), 7.71-7.62 (m, 1H), 7.61-7.50 (m, 3H), 7.35 (dd, J = 8.4, 1.5 Hz, 1H), 7.27-7.15 (m, 1H), 7.14-7.04 (m, 1H), 4.09 (t, J = 6.2 Hz, 2H), 2.75 (t, J = 6.2 Hz, 2H), 2.47-2.34 (m, 7H), 0.84 (t, J = 7.1 Hz, 5H). | 586.2 |
| I-43 | 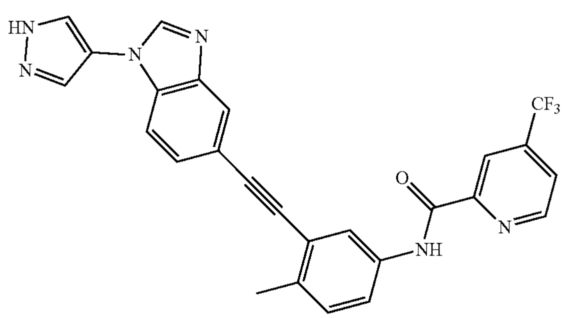 [SMILES: Cc1ccc(NC(=O)c2cc(C(F)(F)F)ccn2)cc1C#Cc1ccc2c(c1)ncn2-c1cn[nH]c1] | (DMSO-d₆): δ 13.34 (s, 1H), 10.84 (s, 1H), 9.05 (dt, J = 5.0, 0.8 Hz, 1H), 8.55 (s, 1H), 8.43-8.33 (m, 2H), 8.18-8.06 (m, 2H), 8.04-7.94 (m, 2H), 7.81 (dd, J = 8.3, 2.3 Hz, 1H), 7.64 (dd, J = 8.4, 0.7 Hz, 1H), 7.57-7.45 (m, 1H), 7.34 (d, J = 8.4 Hz, 1H), 2.50 (s, 3H) | 487.1 |
| I-44 | 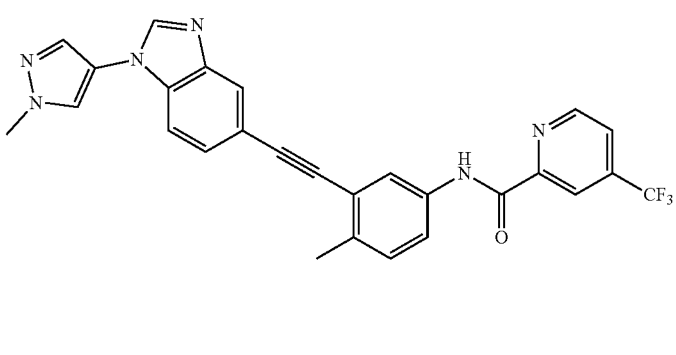 [SMILES: Cc1ccc(NC(=O)c2cc(C(F)(F)F)ccn2)cc1C#Cc1ccc2c(c1)ncn2-c1cnn(C)c1] | (Chloroform-d): δ 9.91 (s, 1H), 8.84 (d, J = 5.02 Hz, 1H), 8.56-8.59 (m, 1H), 8.09 (br, 2H), 7.94 (d, J = 2.26 Hz, 1H), 7.69-7.80 (m, 4H), 7.48-7.61 (m, 1H), 7.36-7.48 (m, 1H), 7.29-7.35 (m, 1H), 4.07 (s, 3H), 2.58 (s, 3H) | 501.1 |

TABLE 1-continued

| Cmpd No. | Compound Structure | ¹H NMR (400 MHz) δ (ppm): | ESI-MS m/z [M + H]⁺ |
|---|---|---|---|
| I-45 | 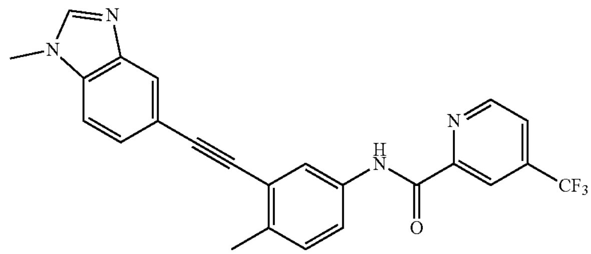 [SMILES: Cc1ccc(NC(=O)c2cc(C(F)(F)F)ccn2)cc1C#Cc1ccc2c(c1)ncn2C] | (Chloroform-d): δ 9.90 (s, 1H), 8.84 (d, J = 5.02 Hz, 1H), 8.58 (s, 1H), 8.05 (br s, 1H), 7.88-8.00 (m, 2H), 7.72-7.78 (m, 2H), 7.54 (d, J = 8.28 Hz, 1H), 7.44 (br s, 1H), 7.30-7.33 (m, 1H), 3.90 (s, 3H), 2.58 (s, 3H) | 435.1 |
| I-46 | 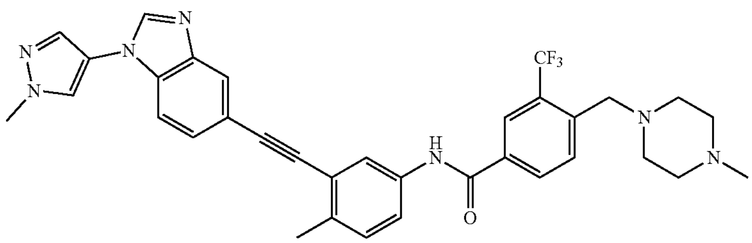 | (Methanol-d₄): 8.40 (s, 1H), 8.26-8.34 (m, 1H), 8.17-8.21 (m, 2H), 8.01 (d, J = 8.16 Hz, 1H), 7.89-7.94 (m, 3), 7.55-7.65 (m, 3H), 7.31 (d, J = 8.41 Hz, 1H), 4.04 (s, 3H), 3.81 (s, 2H), 2.70-2.94 (m, 4H), 2.64 (br s, 4H), 2.55 (s, 3H), 2.44 (s, 3H) | 612.2 |
| I-47 | 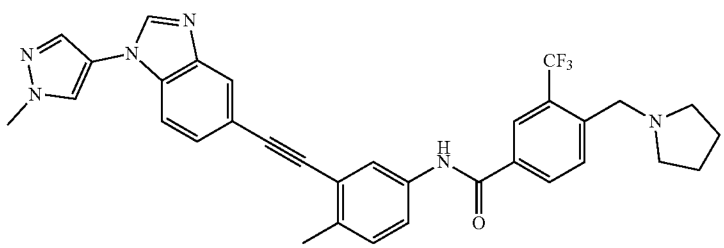 [SMILES: Cc1ccc(NC(=O)c2ccc(CN3CCCC3)c(C(F)(F)F)c2)cc1C#Cc1ccc2c(c1)ncn2-c1cnn(C)c1] | (Methanol-d₄): δ 8.40 (s, 1H), 8.27-8.32 (m, 1H), 8.17-8.22 (m, 2H), 7.89-8.01 (m, 4H), 7.55-7.64 (m, 3H), 7.31 (d, J = 8.41 Hz, 1H), 4.04 (s, 3H), 3.94 (s, 2H), 2.60-2.71 (m, 4H), 2.55 (s, 3H), 1.88 (td, J = 3.25, 6.93 Hz, 4H) | 583.2 |
| I-48 | 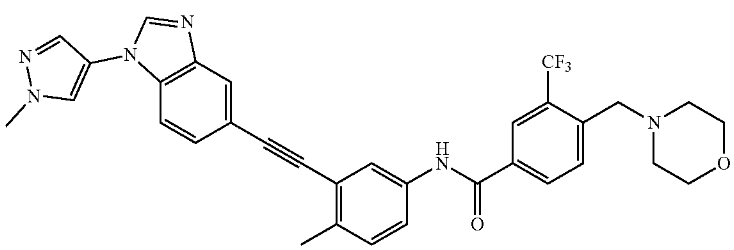 [SMILES: Cc1ccc(NC(=O)c2ccc(CN3CCOCC3)c(C(F)(F)F)c2)cc1C#Cc1ccc2c(c1)ncn2-c1cnn(C)c1] | (Methanol-d₄): δ 8.41 (br s, 1H), 8.24-8.33 (m, 1H), 8.17 (s, 1H), 8.18 (d, J = 7.65 Hz, 1H), 8.03 (d, J = 8.16 Hz, 1H), 7.88-7.95 (m, 3H), 7.53-7.66 (m, 3H), 7.30 (d, J = 8.28 Hz, 1H), 4.03 (s, 3H), 3.74-3.76 (m, 6H), 2.46-2.60 (m, 7H) | 599.2 |
| I-49 | 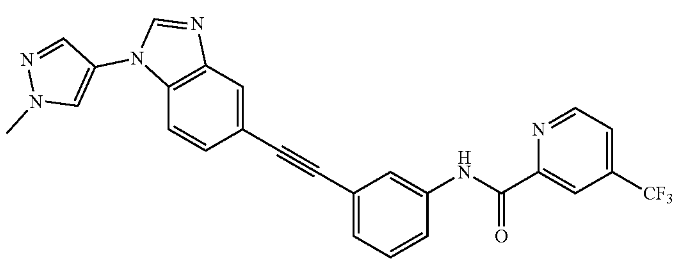 [SMILES: Cn1cc(-n2cnc3cc(C#Cc4cccc(NC(=O)c5cc(C(F)(F)F)ccn5)c4)ccc32)cn1] | (Methanol-d₄): 9.00 (d, J = 5.02 Hz, 1H), 8.48 (s, 1H), 8.40 (s, 1H), 8.18 (s, 1H), 8.10-8.12 (m, 1H), 7.89-7.98 (m, 3H), 7.82 (ddd, J = 1.25, 2.20, 7.97 Hz, 1H), 7.58 (d, J = 1.00 Hz, 2H), 7.37-7.47 (m, 2H), 4.04 (s, 3H) | 487.1 |
| I-50 | 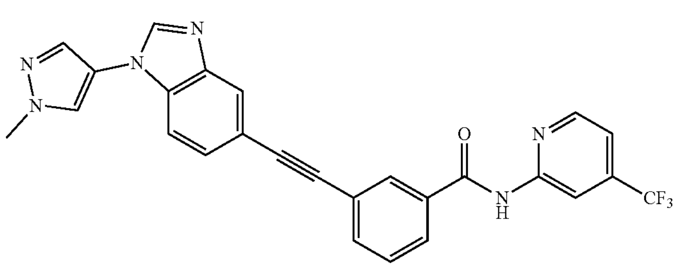 [SMILES: Cn1cc(-n2cnc3cc(C#Cc4cccc(C(=O)Nc5cc(C(F)(F)F)ccn5)c4)ccc32)cn1] | (Methanol-d₄): δ 8.54-8.65 (m, 2H), 8.37 (s, 1H), 8.11-8.20 (m, 2H), 7.97 (d, J = 7.52 Hz, 1H), 7.91 (s, 1H), 7.87 (s, 1H), 7.75 (td, J = 1.27, 7.87 Hz, 1H), 7.51-7.58 (m, 3H), 7.41 (td, J = 1.07, 5.14 Hz, 1H), 4.02 (s, 3H) | 487.1 |

TABLE 1-continued

| Cmpd No. | Compound Structure | $^1$H NMR (400 MHz) δ (ppm): | ESI-MS m/z [M + H]$^+$ |
|---|---|---|---|
| I-51 | (structure) | (Methanol-d$_4$): δ 8.60 (s, 1H), 8.61 (d, J = 5.61 Hz, 1H), 8.41 (s, 1H), 8.27 (dd, J = 2.32, 6.71 Hz, 1H), 8.18 (s, 1H), 8.06 (ddd, J = 2.38, 4.86, 8.69 Hz, 1H), 7.97 (s, 1H), 7.92 (s, 1H), 7.60 (d, J = 0.88 Hz, 2H), 7.43 (d, J = 5.33 Hz, 1H), 7.38 (t, J = 8.96 Hz, 1H), 4.04 (s, 3H) | 505.1 |
| I-52 | (structure) | (DMSO-d$_6$): δ 11.02 (s, 1H), 9.06 (d, J = 5.02 Hz, 1H), 8.48-8.71 (m, 1H), 8.36-8.41 (m, 2H), 8.26 (dd, J = 2.76, 6.53 Hz, 1H), 8.12 (dd, J = 1.13, 5.02 Hz, 1H), 7.94-8.02 (m, 3H), 7.53-7.70 (m, 2H), 7.39 (t, J = 9.10 Hz, 1H), 3.96 (s, 3H) | 505.1 |

$^a$The starting aniline was tert-butyl 4-(4-amino-1H-pyrazol-1-yl)piperidine-1-carboxylate A.
$^b$The starting aniline was 1-tosyl-1H-pyrazol-4-amine B.
A and B are shown below:

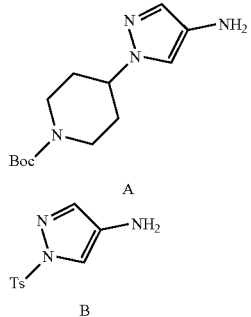

A

B

Biochemical Assays

Example 2: c-Kit Assay

Generation of Ba/F3 KIT Mutant Engineered Cell Lines

KIT cDNAs were synthesized by GenScript and cloned into the pLVX-IRES-Puro vector (Clontech). Viral particles were produced by transfecting pLVX-IRES-puro vectors containing KIT mutant genes into HEK293 cells (Invitrogen) using the Trans-Lentiviral ORF Packaging Kit (Thermo Scientific). 48 hours post-transfection, virus-containing supernatants were harvested and incubated for another 48-72 hours with parental Ba/F3 cells (DSMZ) in the presence of 10 ng/mL L-3 (R&D Systems). Transduced Ba/F3 cells were then selected by IL-3 withdrawal and puromycin (0.5-1 μg/mL, Invitrogen).

Viability Assays

Cell lines (i.e., EX11DEL, EX11DEL/D816H, EX11DEL/T670I, and EX11DEL/V654A) were plated into 384 well plates using RPMI 1640 supplemented with 10% FBS at densities that produced linear growth and incubated at 37° C. in 5% (v/v) CO$_2$. Cells were treated with eight concentrations of compound over a 4-fold dilution (10 μM to 0.61 nM) and viability was assessed using Cell Titer-Glo assay (Promega) after 72 hours. Data were plotted as percent viability relative to vehicle-treated cells. Dose-responses curves were generated and used to calculate IC$_{50}$ values.

Table 2:

c-Kit activity of compounds of the invention in the c-Kit assay. ++++ indicates an IC$_{50}$ of less than about 10 nM, +++ indicates an IC$_{50}$ between about 10 nM and about 50 nM, ++ indicates an IC$_{50}$ between about 50 nM and about 100 nM, and + indicates an IC$_{50}$ greater than about 100 nM and less than about 10 μM.

TABLE 2

| | cKit Assay. | | | |
|---|---|---|---|---|
| Cmpd No. | BAF3 FL KIT EX11DEL (nM) | BAF3 FL KIT EX11DEL/ D816H (nM) | BAF3 FL KIT EX11DEL/ T670I (nM) | BAF3 FL KIT EX11DEL/ V654A (nM) |
| I-1 | ++++ | + | + | + |
| I-2 | ++++ | ++ | +++ | +++ |

TABLE 2-continued cKit Assay.

| Cmpd No. | BAF3 FL KIT EX11DEL (nM) | BAF3 FL KIT EX11DEL/ D816H (nM) | BAF3 FL KIT EX11DEL/ T670I (nM) | BAF3 FL KIT EX11DEL/ V654A (nM) |
|---|---|---|---|---|
| I-3 | ++ | + | + | + |
| I-4 | ++++ | + | ++ | ++ |
| I-5 | ++ | + | + | + |
| I-6 | +++ | + | ++ | + |
| I-7 | +++ | + | ++ | + |
| I-8 | +++ | ++ | +++ | +++ |
| I-9 | +++ | + | + | + |
| I-10 | +++ | + | + | + |
| I-11 | + | + | + | + |
| I-12 | +++ | + | + | + |
| I-13 | +++ | + | + | + |
| I-14 | ++ | + | + | + |
| I-15 | ++ | + | + | + |
| I-16 | +++ | + | + | + |
| I-17 | +++ | ++ | +++ | +++ |
| I-18 | + | + | + | + |
| I-19 | ++++ | +++ | ++++ | +++ |
| I-20 | +++ | + | + | + |
| I-21 | + | + | + | + |
| I-22 | + | + | + | + |
| I-23 | ++++ | +++ | ++++ | +++ |
| I-24 | ++++ | +++ | ++++ | +++ |
| I-25 | ++++ | +++ | ++++ | +++ |
| I-26 | ++++ | +++ | +++ | +++ |
| I-27 | ++++ | +++ | +++ | +++ |
| I-28 | +++ | ++ | +++ | ++ |
| I-29 | +++ | +++ | +++ | ++ |
| I-30 | +++ | + | ++ | ++ |
| I-31 | ++++ | +++ | ++++ | +++ |
| I-32 | ++++ | +++ | ++++ | +++ |
| I-33 | ++++ | +++ | ++++ | +++ |
| I-34 | ++++ | + | +++ | + |
| I-35 | ++++ | +++ | +++ | +++ |
| I-36 | ++++ | +++ | +++ | +++ |
| I-37 | ++++ | +++ | +++ | ++ |
| I-38 | ++++ | ++ | +++ | +++ |
| I-39 | ++++ | +++ | ++++ | +++ |
| I-40 | ++++ | + | +++ | + |
| I-41 | ++++ | + | +++ | ++ |
| I-42 | +++ | + | +++ | ++ |
| I-43 | ++++ | ++ | ++ | + |
| I-44 | ++++ | +++ | +++ | +++ |
| I-45 | +++ | ++ | +++ | ++ |
| I-46 | +++ | + | ++ | + |
| I-47 | +++ | + | ++ | + |
| I-48 | ++++ | ++ | +++ | ++ |
| I-49 | ++++ | + | +++ | ++ |
| I-50 | ++++ | + | ++++ | ++ |
| I-51 | ++++ | + | ++++ | +++ |
| I-52 | ++++ | + | ++++ | ++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound having one of the following formulae (Ii) or (Ij):

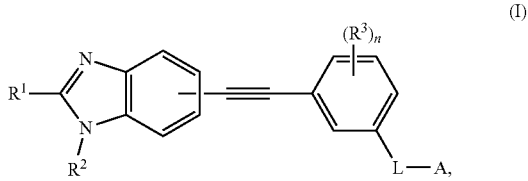

(I)

or a pharmaceutically acceptable salt thereof, wherein:

$R^1$ is H, $(C_1-C_6)$ alkylamino, or $(C_1-C_6)$ dialkylamino;

$R^2$ is H, $(C_1-C_6)$ alkyl, —$(C(R^{6a})_2)_p$—$(C_3-C_7)$ cycloalkyl, —$(C(R^{6a})_2)_p$-heterocycloalkyl wherein the heterocycloalkyl comprises a 4- to 7-membered ring and 1 to 3 heteroatoms selected from N, O, and S, —$(C(R^{6a})_2)_p$—$(C_6-C_{10})$ aryl, or —$(C(R^{6a})_2)_p$-heteroaryl wherein the heteroaryl comprises a 5- or 6-membered ring and 1 to 3 heteroatoms selected from N, O, and S, wherein the alkyl is optionally substituted with one or more $R^7$, wherein the cycloalkyl, heterocycloalkyl, aryl, or heteroaryl is optionally substituted with one or more $R^9$;

each $R^3$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or OH;

each $R^4$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, CN, $(C_3-C_7)$ cycloalkyl, —$(C(R^{6b})_2)_q$—$NH_2$, —$(C(R^{6b})_2)_q$—$(C_1-C_6)$ alkylamino, —$(C(R^{6b})_2)_q$—$(C_1-C_6)$ dialkylamino, —$(C(R^{6b})_2)_q$-heterocycloalkyl wherein the heterocycloalkyl comprises a 4- to 7-membered ring and 1 to 3 heteroatoms selected from N, O, and S, or —$(C(R^{6b})_2)_q$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from $(C_1-C_6)$ alkyl, —$NH_2$, $(C_1-C_6)$ alkylamino, and $(C_1-C_6)$ dialkylamino;

$R^5$ is H, $(C_1-C_6)$ alkyl, or $(C_1-C_6)$ haloalkyl;

each $R^{6a}$ and $R^{6b}$ is independently H or $(C_1-C_6)$ alkyl;

$R^7$ is $(C_1-C_6)$ alkoxy, $(C_1-C_6)$ haloalkoxy, —OH, —$NH_2$, $(C_1-C_6)$ alkylamino, $(C_1-C_6)$ dialkylamino, or —$C(O)N(R^8)_2$;

each $R^8$ is independently H, $(C_1-C_6)$ alkyl, or $(C_1-C_6)$ haloalkyl;

each $R^9$ is independently at each occurrence $(C_1-C_6)$ alkyl, $(C_1-C_6)$ haloalkyl, —$C(O)H$, —$C(O)(C_1-C_6)$ alkyl, or 5- to 7-membered heterocycloalkyl ring comprising 1 to 3 heteroatoms selected from N, O and S, wherein the heterocycloalkyl is optionally substituted with one or more substituents each independently selected from $(C_1-C_6)$ alkyl, —$C(O)H$, or —$C(O)(C_1-C_6)$ alkyl, and wherein the alkyl is optionally substituted with one or more substituents each independently selected from $(C_1-C_6)$ alkoxy, —OH, $(C_1-C_6)$ haloalkoxy, —$NH_2$, $(C_1-C_6)$ alkylamino, or $(C_1-C_6)$ dialkylamino; and each n, p, and q is independently 0, 1 or 2.

2. The compound of claim 1, having the formulae (Ii):

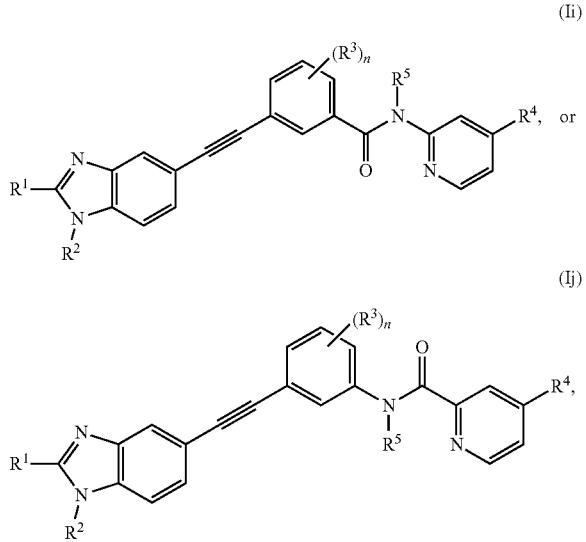

or a pharmaceutically acceptable salt thereof.

3. The compound of claim 1, wherein $R^5$ is H.
4. The compound of claim 1, wherein $R^4$ is $(C_1$-$C_6)$ haloalkyl.
5. The compound of claim 1, wherein n is 1, $R^3$ is methyl, $R^1$ is H, and $R^2$ is H; $CH_3$; $CH_2CH_3$; —$(CH_2)_2N(CH_3)_2$; —$(CH_2)_3N(CH_3)_2$; —$CH_2C(O)NH(CH_3)$;
—$(CH_2)_2$morpholinyl; —$(CH_2)_2OCH_3$; piperidinyl substituted with methyl; phenyl optionally substituted with 4-methylpiperazine; —$CH_2$-pyridinyl; cyclopropyl; triazolyl substituted with methyl; or imidazolyl substituted with methyl or N-methyl piperidinyl; or n is 1 and $R^3$ is methyl, $R^1$ is pyrazolyl optionally substituted with methyl; —$(CH_2)_2OH$; —$(CH_2)_2OCH_3$; —$(CH_2)_2N(CH_3)_2$; —$(CH_2)_2N(CH_2CH_3)_2$; morpholinyl; or piperidinyl optionally substituted with methyl or —C(O)H; or n is 0 or 1 and $R^3$ is F, $R^1$ is pyrazolyl optionally substituted with methyl; or n is 1, $R^3$ is methyl, $R^1$ is $NH_2$ and $R^2$ is H.

6. A compound selected from the group consisting of:
4-methyl-3-((1-(2-(methylamino)-2-oxoethyl)-1H-benzo[d]imidazol-5-yl)ethynyl)-N-(4-(trifluoromethyl)pyridin-2-yl)benzamide (1-1);
3-((1H-benzo[d]imidazol-5-yl)ethynyl)-4-methyl-N-(4-(trifluoromethyl)pyridin-2-yl)benzamide (1-2);
3-((1-(2-(dimethylamino)ethyl)-1H-benzo[d]imidazol-5-yl)ethynyl)-4-methyl-N-(4-(trifluoromethyl)pyridin-2-yl)benzamide (1-3);
3-((1-(2-methoxyethyl)-1H-benzo[d]imidazol-5-yl)ethynyl)-4-methyl-N-(4-(trifluoromethyl)pyridin-2-yl)benzamide (1-4);
4-methyl-3-((1-(2-morpholinoethyl)-1H-benzo[d]imidazol-5-yl)ethynyl)-N-(4-(trifluoromethyl)pyridin-2-yl)benzamide (1-5);
3-((1-(3-(dimethylamino)propyl)-1H-benzo[d]imidazol-5-yl)ethynyl)-4-methyl-N-(4-(trifluoromethyl)pyridin-2-yl)benzamide (1-6);
3-((1-ethyl-1H-benzo[d]imidazol-5-yl)ethynyl)-4-methyl-N-(4-(trifluoromethyl)pyridin-2-yl)benzamide (I-7);
4-methyl-3-((1-methyl-1H-benzo[d]imidazol-5-yl)ethynyl)-N-(4-(trifluoromethyl)pyridin-2-yl)benzamide (1-8);
3-((2-amino-1H-benzo[d]imidazol-6-yl)ethynyl)-4-methyl-N-(4-(trifluoromethyl)pyridin-2-yl)benzamide (1-10);
4-methyl-3-((1-methyl-1H-benzo[d]imidazol-6-yl)ethynyl)-N-(4-(trifluoromethyl)pyridin-2-yl)benzamide (1-11);
4-methyl-3-((1-(pyridin-3-ylmethyl)-1H-benzo[d]imidazol-5-yl)ethynyl)-N-(4-(trifluoromethyl)pyridin-2-yl)benzamide (1-12);
3-((1-cyclopropyl-1H-benzo[d]imidazol-5-yl)ethynyl)-4-methyl-N-(4-(trifluoromethyl)pyridin-2-yl)benzamide (1-13);
4-methyl-3-((1-(3-(4-methylpiperazin-1-yl)phenyl)-1H-benzo[d]imidazol-5-yl)ethynyl)-N-(4-(trifluoromethyl)pyridin-2-yl)benzamide (1-14);
4-methyl-3-((1-(4-(4-methylpiperazin-1-yl)phenyl)-1H-benzo[d]imidazol-5-yl)ethynyl)-N-(4-(trifluoromethyl)pyridin-2-yl)benzamide (1-15);
4-methyl-3-((1-(1-methyl-1H-pyrazol-4-yl)-1H-benzo[d]imidazol-5-yl)ethynyl)-N-(4-(trifluoromethyl)pyridin-2-yl)benzamide (1-17);
N-(4-methyl-3-((1-methyl-1H-benzo[d]imidazol-5-yl)ethynyl)phenyl)-4-((4-methylpiperazin-1-yl)methyl)-3-(trifluoromethyl)benzamide (1-18);
4-methyl-3-((1-(1-methyl-1H-pyrazol-4-yl)-1H-benzo[d]imidazol-5-yl)ethynyl)-N-(4-(trifluoromethyl)pyridin-2-yl)benzamide (1-19);
4-methyl-3-((1-(1-methylpiperidin-4-yl)-1H-benzo[d]imidazol-5-yl)ethynyl)-N-(4-(trifluoromethyl)pyridin-2-yl)benzamide (1-20);
4-methyl-3-((1-phenyl-1H-benzo[d]imidazol-5-yl)ethynyl)-N-(4-(trifluoromethyl)pyridin-2-yl)benzamide (1-21);
4-methyl-3-((1-methyl-1H-benzo[d]imidazol-5-yl)ethynyl)-N-(4-(4-methylpiperazin-1-yl)-3-(trifluoromethyl)phenyl)benzamide (1-22);
4-methyl-3-((1-(1-methyl-1H-imidazol-4-yl)-1H-benzo[d]imidazol-5-yl)ethynyl)-N-(4-(trifluoromethyl)pyridin-2-yl)benzamide (1-23);
4-methyl-3-((1-(1-methyl-1H-1,2,3-triazol-4-yl)-1H-benzo[d]imidazol-5-yl)ethynyl)-N-(4-(trifluoromethyl)pyridin-2-yl)benzamide (1-24);
3-((1-(1-(1-formylpiperidin-4-yl)-1H-pyrazol-4-yl)-1H-benzo[d]imidazol-5-yl)ethynyl)-4-methyl-N-(4-(trifluoromethyl)pyridin-2-yl)benzamide (1-25);
4-methyl-3-((1-(1-(piperidin-4-yl)-1H-pyrazol-4-yl)-1H-benzo[d]imidazol-5-yl)ethynyl)-N-(4-(trifluoromethyl)pyridin-2-yl)benzamide (1-26);
4-methyl-3-((1-(1-(1-methylpiperidin-4-yl)-1H-pyrazol-4-yl)-1H-benzo[d]imidazol-5-yl)ethynyl)-N-(4-(trifluoromethyl)pyridin-2-yl)benzamide (1-27);
N-(3-cyclopropylphenyl)-4-methyl-3-((1-(1-methyl-1H-pyrazol-4-yl)-1H-benzo[d]imidazol-5-yl)ethynyl)benzamide (1-28);
4-methyl-3-((1-(1-methyl-1H-pyrazol-4-yl)-1H-benzo[d]imidazol-5-yl)ethynyl)-N-(4-(pyrrolidin-1-ylmethyl)-3-(trifluoromethyl)phenyl)benzamide (1-29);
4-methyl-3-((1-methyl-1H-benzo[d]imidazol-5-yl)ethynyl)-N-(4-(pyrrolidin-1-ylmethyl)-3-(trifluoromethyl)phenyl)benzamide (1-30);
3-((1-(1-(2-hydroxyethyl)-1H-pyrazol-4-yl)-1H-benzo[d]imidazol-5-yl)ethynyl)-4-methyl-N-(4-(trifluoromethyl)pyridin-2-yl)benzamide (1-31);

3-((1-(1-(2-methoxyethyl)-1H-pyrazol-4-yl)-1H-benzo[d]imidazol-5-yl)ethynyl)-4-methyl-N-(4-(trifluoromethyl)pyridin-2-yl)benzamide (1-32);

4-methyl-3-((1-(1-(tetrahydro-2H-pyran-4-yl)-1H-pyrazol-4-yl)-1H-benzo[d]imidazol-5-yl)ethynyl)-N-(4-(trifluoromethyl)pyridin-2-yl)benzamide (1-33);

4-methyl-3-((1-(1-(1-methylpiperidin-4-yl)-1H-imidazol-4-yl)-1H-benzo[d]imidazol-5-yl)ethynyl)-N-(4-(trifluoromethyl)pyridin-2-yl)benzamide (1-34);

3-((1-(1H-pyrazol-4-yl)-1H-benzo[d]imidazol-5-yl)ethynyl)-4-methyl-N-(4-(trifluoromethyl)pyridin-2-yl)benzamide (1-35);

N-(4-methyl-3-((1-(1-methyl-1H-1,2,3-triazol-4-yl)-1H-benzo[d]imidazol-5-yl)ethynyl)phenyl)-4-(trifluoromethyl)picolinamide (1-36);

N-(4-cyano-3-(trifluoromethyl)phenyl)-4-methyl-3-((1-(1-methyl-1H-pyrazol-3-yl)-1H-benzo[d]imidazol-5-yl)ethynyl)benzamide (1-37);

N-(3-((1-(1-(2-methoxyethyl)-1H-pyrazol-4-yl)-1H-benzo[d]imidazol-5-yl)ethynyl)-4-methylphenyl)-4-(trifluoromethyl)picolinamide (1-38);

N-(3-((1-(1-(2-hydroxyethyl)-1H-pyrazol-4-yl)-1H-benzo[d]imidazol-5-yl)ethynyl)-4-methylphenyl)-4-(trifluoromethyl)picolinamide (1-39);

N-(3-((1-(1-(2-hydroxyethyl)-1H-pyrazol-4-yl)-1H-benzo[d]imidazol-5-yl)ethynyl)-4-methylphenyl)-4-(trifluoromethyl)picolinamide (1-40);

N-(3-((1-(1-(2-(dimethylamino)ethyl)-1H-pyrazol-4-yl)-1H-benzo[d]imidazol-5-yl)ethynyl)-4-methylphenyl)-4-(trifluoromethyl)picolinamide (1-41);

N-(3-((1-(1-(2-(diethylamino)ethyl)-1H-pyrazol-4-yl)-1H-benzo[d]imidazol-5-yl)ethynyl)-4-methylphenyl)-4-(trifluoromethyl)picolinamide (1-42);

N-(3-((1-(1H-pyrazol-4-yl)-1H-benzo[d]imidazol-5-yl)ethynyl)-4-methylphenyl)-4-(trifluoromethyl)picolinamide (1-43);

N-(4-methyl-3-((1-(1-methyl-1H-pyrazol-4-yl)-1H-benzo[d]imidazol-5-yl)ethynyl)phenyl)-4-(trifluoromethyl)picolinamide (1-44);

N-(4-methyl-3-((1-methyl-1H-benzo[d]imidazol-5-yl)ethynyl)phenyl)-4-(trifluoromethyl)picolinamide (I-45);

N-(4-methyl-3-((1-(1-methyl-1H-pyrazol-4-yl)-1H-benzo[d]imidazol-5-yl)ethynyl)phenyl)-4-((4-methylpiperazin-1-yl)methyl)-3-(trifluoromethyl)benzamide (1-46);

N-(4-methyl-3-((1-(1-methyl-1H-pyrazol-4-yl)-1H-benzo[d]imidazol-5-yl)ethynyl)phenyl)-4-(pyrrolidin-1-ylmethyl)-3-(trifluoromethyl)benzamide (1-47);

N-(4-methyl-3-((1-(1-methyl-1H-pyrazol-4-yl)-1H-benzo[d]imidazol-5-yl)ethynyl)phenyl)-4-(morpholinomethyl)-3-(trifluoromethyl)benzamide (1-48);

N-(3-((1-(1-methyl-1H-pyrazol-4-yl)-1H-benzo[d]imidazol-5-yl)ethynyl)phenyl)-4-(trifluoromethyl)picolinamide (1-49);

3-((1-(1-methyl-1H-pyrazol-4-yl)-1H-benzo[d]imidazol-5-yl)ethynyl)-N-(4-(trifluoromethyl)pyridin-2-yl)benzamide (1-50);

4-fluoro-3-((1-(1-methyl-1H-pyrazol-4-yl)-1H-benzo[d]imidazol-5-yl)ethynyl)-N-(4-(trifluoromethyl)pyridin-2-yl)benzamide (1-51); and N-(4-fluoro-3-((1-(1-methyl-1H-pyrazol-4-yl)-1H-benzo[d]imidazol-5-yl)ethynyl)phenyl)-4-(trifluoromethyl)picolinamide (I-52), or a pharmaceutically acceptable salt thereof.

7. The compound of claim 1, having the formula (Ij):

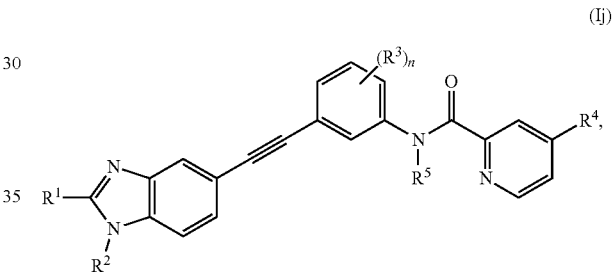

or a pharmaceutically acceptable salt thereof.

* * * * *

UNITED STATES PATENT AND TRADEMARK OFFICE
CERTIFICATE OF CORRECTION

PATENT NO. : 11,117,883 B2
APPLICATION NO. : 16/469535
DATED : September 14, 2021
INVENTOR(S) : Bencivenga et al.

Page 1 of 4

It is certified that error appears in the above-identified patent and that said Letters Patent is hereby corrected as shown below:

In the Claims

In Claim 1, Column 66, Delete structure at Lines 5 through 14 and replace it with

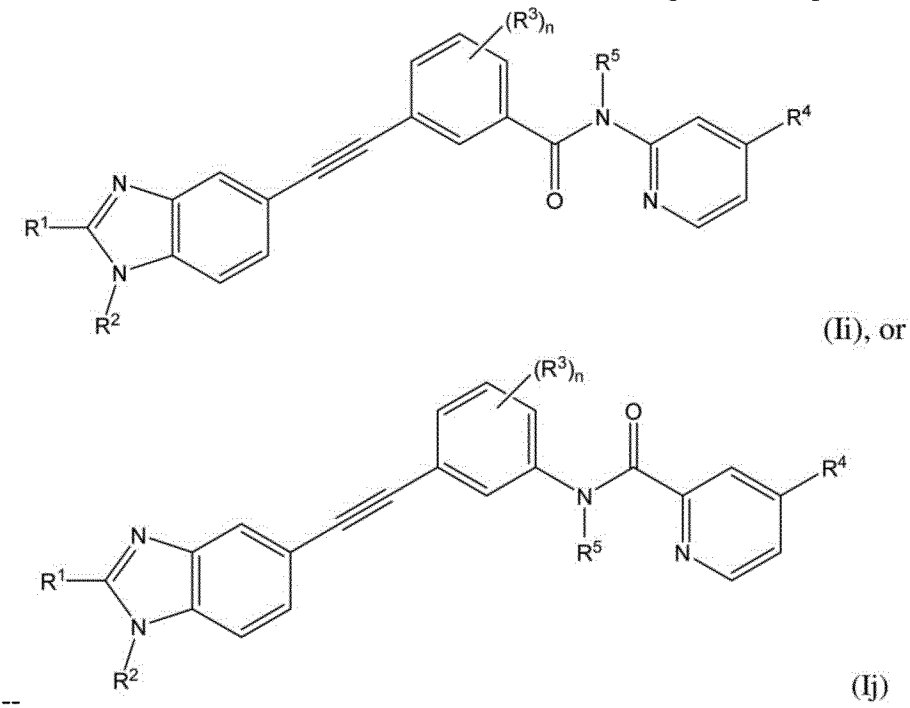

In Claim 1, Column 66, Line 20, Delete "and Ito 3" and replace it with --and 1 to 3--

In Claim 2, Column 67, Line 8, Delete "or"

In Claim 2, Column 67, Delete structure at Lines 13 through 24

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*

In Claim 6, Column 67, Line 50, Delete "(1-1)" and replace with --(I-1)--

In Claim 6, Column 67, Line 52, Delete "(1-2)" and replace with --(I-2)--

In Claim 6, Column 67, Line 55, Delete "(1-3)" and replace with --(I-3)--

In Claim 6, Column 67, Line 58, Delete "(1-4)" and replace with --(I-4)--

In Claim 6, Column 67, Line 61, Delete "(1-5)" and replace with --(I-5)--

In Claim 6, Column 67, Line 64, Delete "(1-6)" and replace with --(I-6)--

In Claim 6, Column 68, Line 3, Delete "(1-8)" and replace with --(I-8)--

In Claim 6, Column 68, Line 6, Delete "(1-10)" and replace with --(I-10)--

In Claim 6, Column 68, Line 9, Delete "(1-11)" and replace with --(I-11)--

In Claim 6, Column 68, Line 12, Delete "(1-12)" and replace with --(I-12)--

In Claim 6, Column 68, Line 15, Delete "(1-13)" and replace with --(I-13)--

In Claim 6, Column 68, Line 18, Delete "(1-14)" and replace with --(I-14)--

In Claim 6, Column 68, Line 21, Delete "(1-15)" and replace with --(I-15)--

In Claim 6, Column 68, Line 24, Delete "(1-17)" and replace with --(I-17)--

In Claim 6, Column 68, Line 27, Delete "(1-18)" and replace with --(I-18)--

In Claim 6, Column 68, Line 30, Delete "(1-19)" and replace with --(I-19)--

In Claim 6, Column 68, Line 33, Delete "(1-20)" and replace with --(I-20)--

In Claim 6, Column 68, Line 36, Delete "(1-21)" and replace with --(I-21)--

In Claim 6, Column 68, Line 39, Delete "(1-22)" and replace with --(I-22)--

In Claim 6, Column 68, Line 42, Delete "(1-23)" and replace with --(I-23)--

In Claim 6, Column 68, Line 45, Delete "(1-24)" and replace with --(I-24)--

In Claim 6, Column 68, Line 48, Delete "(1-25)" and replace with --(I-25)--

CERTIFICATE OF CORRECTION (continued)
U.S. Pat. No. 11,117,883 B2

In Claim 6, Column 68, Line 51, Delete "(1-26)" and replace with --(I-26)--

In Claim 6, Column 68, Line 54, Delete "(1-27)" and replace with --(I-27)--

In Claim 6, Column 68, Line 57, Delete "(1-28)" and replace with --(I-28)--

In Claim 6, Column 68, Line 60, Delete "(1-29)" and replace with --(I-29)--

In Claim 6, Column 68, Line 63, Delete "(1-30)" and replace with --(I-30)--

In Claim 6, Column 68, Line 66, Delete "(1-31)" and replace with --(I-31)--

In Claim 6, Column 69, Line 3, Delete "(1-32)" and replace with --(I-32)--

In Claim 6, Column 69, Line 6, Delete "(1-33)" and replace with --(I-33)--

In Claim 6, Column 69, Line 9, Delete "(1-34)" and replace with --(I-34)--

In Claim 6, Column 69, Line 12, Delete "(1-35)" and replace with --(I-35)--

In Claim 6, Column 69, Line 15, Delete "(1-36)" and replace with --(I-36)--

In Claim 6, Column 69, Line 18, Delete "(1-37)" and replace with --(I-37)--

In Claim 6, Column 69, Line 21, Delete "(1-38)" and replace with --(I-38)--

In Claim 6, Column 69, Line 24, Delete "(1-39)" and replace with --(I-39)--

In Claim 6, Column 69, Line 27, Delete "(1-40)" and replace with --(I-40)--

In Claim 6, Column 69, Line 30, Delete "(1-41)" and replace with --(1-41)--

In Claim 6, Column 69, Line 33, Delete "(1-42)" and replace with --(I-42)--

In Claim 6, Column 69, Line 36, Delete "(1-43)" and replace with --(I-43)--

In Claim 6, Column 69, Line 39, Delete "(1-44)" and replace with --(I-44)--

In Claim 6, Column 70, Line 4, Delete "(1-46)" and replace with --(I-46)--

In Claim 6, Column 70, Line 7, Delete "(1-47)" and replace with --(I-47)--

In Claim 6, Column 70, Line 10, Delete "(1-48)" and replace with --(I-48)--

CERTIFICATE OF CORRECTION (continued)
U.S. Pat. No. 11,117,883 B2

In Claim 6, Column 70, Line 13, Delete "(1-49)" and replace with --(I-49)--

In Claim 6, Column 70, Line 16, Delete "(1-50)" and replace with --(I-50)--

In Claim 6, Column 70, Line 19, Delete "(1-51)" and replace with --(I-51)--